US012564334B2

(12) United States Patent
Sukumaran et al.

(10) Patent No.: US 12,564,334 B2
(45) Date of Patent: Mar. 3, 2026

(54) PATIENT SUPPORT APPARATUS WITH CAREGIVER REMINDERS

(71) Applicant: Stryker Corporation, Kalamazoo, MI (US)

(72) Inventors: Sujay Sukumaran, Portage, MI (US); Celso Henrique Farnese Pires Pereira, Portage, MI (US); Kurosh Nahavandi, Portage, MI (US); Placide Nibakuze, Kalamazoo, MI (US); Grady Sertic, St. Louis, MO (US); Krishna Sandeep Bhimavarapu, Kalamazoo, MI (US); Anish Paul, Portage, MI (US); Madhu Sandeep Thota, Portage, MI (US); Zane Marwan Shami, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 131 days.

(21) Appl. No.: 18/561,459

(22) PCT Filed: May 24, 2022

(86) PCT No.: PCT/US2022/030706
§ 371 (c)(1),
(2) Date: Nov. 16, 2023

(87) PCT Pub. No.: WO2022/251199
PCT Pub. Date: Dec. 1, 2022

(65) Prior Publication Data
US 2024/0245319 A1     Jul. 25, 2024

Related U.S. Application Data

(60) Provisional application No. 63/193,780, filed on May 27, 2021.

(51) Int. Cl.
*A61B 5/11* (2006.01)
*A61B 5/00* (2006.01)

(52) U.S. Cl.
CPC ............ *A61B 5/1115* (2013.01); *A61B 5/746* (2013.01)

(58) Field of Classification Search
CPC ......... A61B 5/00; A61B 5/002; A61B 5/0022; A61B 5/0077; A61B 5/11; A61B 5/1115;
(Continued)

(56) References Cited

U.S. PATENT DOCUMENTS 5,276,432 A     1/1994   Travis
7,253,366 B2    8/2007   Bhai
(Continued)

FOREIGN PATENT DOCUMENTS

WO       2020102129 A1     5/2020
WO       2020257475 A1     12/2020

OTHER PUBLICATIONS

Jahne-Raden et al., INBED: A Higly Specialized System for Bed-Exit-Detection and Fall Prevention on a Geriatric Ward, Sensors, Feb. 27, 2019, 23 pages, MDPI.

*Primary Examiner* — Van T Trieu
(74) *Attorney, Agent, or Firm* — Gardner, Linn, Burkhart & Ondersma LLP

(57) ABSTRACT

A patient support apparatus, such as a bed, cot, stretcher, operating table, recliner, or the like, includes a patient support structure, a user interface, a display, and a controller. The user interface comprises a display and controls for configuring various components of the patient support apparatus. The patient support apparatus includes an exit detection system and a monitoring system, and each system may be separately armed and disarmed. The controller uses the display to issue one or more reminders to the caregiver to put (Continued)

the patient support apparatus in a desired configuration before the caregiver walks away from the patient support apparatus. Reminders may be ignored or dismissed. If a reminder is dismissed, the reminder is turned off for that patient and the corresponding system is disarmed. A caregiver may re-enable a reminder after it has been turned off.

14 Claims, 11 Drawing Sheets

(58) Field of Classification Search
CPC ....... A61B 5/7275; A61B 5/743; A61B 5/744; A61B 5/746; A61G 7/05; G16H 10/60; G16H 40/20; G16H 40/67
See application file for complete search history.

(56) References Cited

U.S. PATENT DOCUMENTS

| | | |
|---|---|---|
| 10,617,327 B2 | 4/2020 | Kostic et al. |
| 10,786,408 B2 | 9/2020 | Sidhu et al. |
| 10,898,400 B2 | 1/2021 | Kostic et al. |
| 2011/0205061 A1 | 8/2011 | Wilson et al. |
| 2014/0343968 A1 | 11/2014 | Wilson et al. |
| 2015/0323388 A1 | 11/2015 | Kostic et al. |
| 2017/0176240 A1 | 6/2017 | Paul et al. |
| 2018/0303687 A1 | 10/2018 | Moreno et al. |
| 2021/0045951 A1 | 2/2021 | Nahavandi et al. |
| 2021/0052197 A1 | 2/2021 | Sukumaran et al. |
| 2021/0251579 A1 | 8/2021 | Nahavandi et al. |
| 2021/0353179 A1 | 11/2021 | Sukumaran et al. |
| 2022/0122724 A1* | 4/2022 | Durlach ................. A61B 5/002 |
| 2023/0233102 A1 | 7/2023 | Paul et al. |
| 2023/0371815 A1* | 11/2023 | Nave ................... A61B 5/1079 |

* cited by examiner

156

Brake Off

Turn on now?

160  Ignore | Turn Brakes On  158

162

Nurse Call Unplugged

Check connection

164  Ignore

166

Bed Unplugged

Plug bed back in

168  Ignore

170

Communication Issue

Wireless Connection Issue

172  Ignore

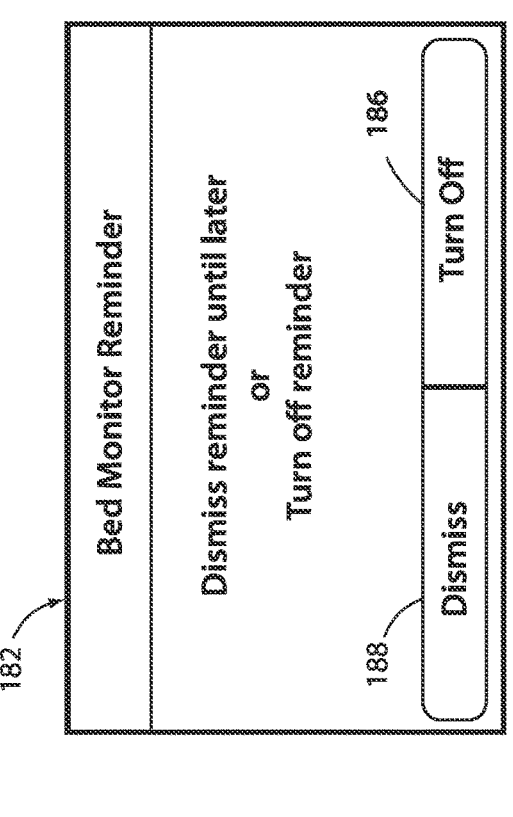
FIG. 9
FIG. 10
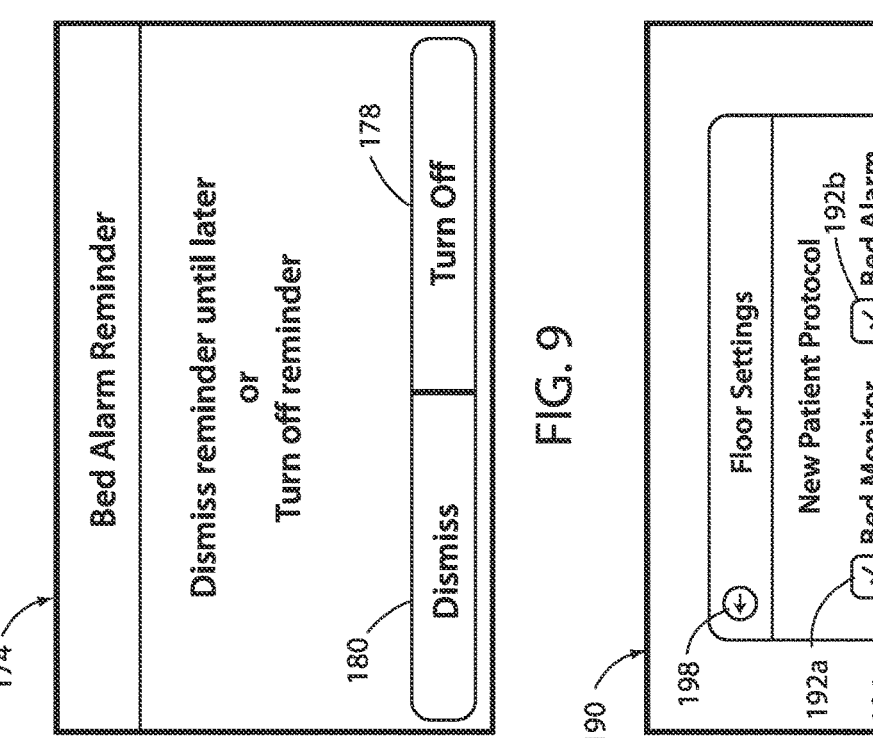
FIG. 11

PATIENT SUPPORT APPARATUS WITH CAREGIVER REMINDERS

CROSS REFERENCE TO RELATED APPLICATIONS

The application claims priority to and all advantages of U.S. Provisional Patent Application No. 63/193,780 filed on 27 May 2021, the content of which is incorporated herein by reference.

BACKGROUND

The present disclosure relates to patient support apparatuses, such as beds, cots, stretchers, operating tables, recliners, or the like. More specifically, the present disclosure relates to patient support apparatuses that include various reminder functions.

Conventional patient support apparatuses comprise a base, a litter frame, a support deck upon which the patient is supported, a lift system for lifting and lowering the litter frame relative to the base, and an articulation system for articulating one or more sections of the support deck. Control of these and other systems of the patient support apparatus is performed via a user interface provided on a footboard or on one or more of the side rails of the patient support apparatus. Often, operation of the user interface is complex, making the user interface difficult to operate.

Most healthcare facilities expect their caregivers to ensure that the patient support apparatuses are configured in a particular manner (e.g. one or more components are in a desired state). These expectations are in addition to the caregiver's many other responsibilities, and in many instances the duty of ensuring the patient support apparatuses are properly configured may be overlooked and/or forgotten.

SUMMARY

According to various aspects, an improved patient support apparatus is provided that is configured to provide reminders to the caregiver in order to assist the caregiver in configuring the patient support apparatus in a desired manner before the caregiver exits from the room in which the patient support apparatus is positioned. The reminders may be issued in multiple manners, including an initial, reminder screen that is shown on a display of the patient support apparatus. In some embodiments, the patient support apparatus may be configured to implement both patient-specific reminders that apply only to the specific patient currently assigned to the patient support apparatus and global reminders that apply to all patients that are assigned to the patient support apparatus. By managing these different types of reminders, the patient support apparatus automatically assists the caregiver in ensuring that, if a reminder is turned off for a particular patient, it is not turned off for all patients. Further, the patient support apparatus may be configured to automatically turn on the patient-specific reminder in response to the caregiver arming the exit detection system, thereby ensuring that reminders are automatically issued for that patient in the future.

According to one aspect of the present disclosure, a patient support apparatus is provided that includes a support surface, a display, an exit detection system, a memory, a reminder control, an arming control, and a controller. The support surface is adapted to support a patient thereon. The exit detection system is adapted to be armed and disarmed, and to issue an exit alert when the patient exits from the patient support apparatus while the exit detection system is armed. The memory includes a first setting and a second setting stored therein. The first setting indicates whether a reminder to arm the exit detection system is to be issued for all patients and the second setting indicates whether the reminder is to be issued for a specific patient. Each of the first and second settings are adapted to be in an on state in which the reminder is issued and an off state in which the reminder is not issued. The reminder control is adapted to allow a user to change the first setting between the on state and the off state. The arming control is adapted to arm and disarm the exit detection system. The controller is configured to detect when a patient is present on the support surface and to display the reminder on the display if the first setting is in the on state and the exit detection system is not armed. The controller is further adapted to not display the reminder on the display if the second setting is in the off state.

According to other aspects, when both the first and second settings are in the off state, the controller is adapted not to display the reminder. When both the first and second settings are in the on state, the controller is adapted to display the reminder.

In some aspects, the controller is further adapted to display the reminder if the first setting is in the off state and the second setting is in the on state, and to not display the reminder if the first setting is in the on state and the second setting is in the off state. The user is able to turn the second setting on and off for a given patient.

In some aspects, the reminder includes a first option to dismiss the reminder and a second option to turn off the reminder. The controller is adapted to remove the reminder when a user selects the first option but to leave the first and second settings unchanged. When a user selects the second option, the controller is adapted to remove the reminder and set the second setting to the off state.

In some aspects, the arming control automatically switches the second setting to the on state when the exit detection system is armed.

In some aspects, the reminder control automatically switches the second setting to the off state when the first setting is set to the off state.

In some aspects, the patient support apparatus includes a new patient control. When activated, the new patient control is configured to leave the first setting unchanged and automatically change the second setting to the same state as the first setting. The new patient control may also erase patient-specific data stored in memory when the new patient control is activated.

According to another aspect of the disclosure, the patient support apparatus further includes an audio playback circuit in communication with the controller. The audio playback circuit stores at least one audio file used to alert hospital staff if the exit detection system is triggered. An amplifier is in communication with the audio playback circuit and the amplifier increases the volume of the audio file. The amplifier is connected to a speaker which emits the audio file to alert a caregiver that the exit detection system has been triggered.

According to another aspect of the present disclosure, a patient support apparatus is provided that includes a support surface, a display, a monitoring system, a memory, a reminder control, an arming control, and a controller. The support surface is adapted to support a patient thereon. The monitoring system is adapted to monitor, when armed, a plurality of components onboard the patient support apparatus and to issue a monitoring alert if any one or more of the plurality of components are in an undesired state. The memory includes a first setting and a second setting stored therein. The first setting indicates whether a reminder to arm the monitoring system is to be issued for all patients and the second setting indicates whether the reminder is to be issued for a specific patient. Each of the first and second settings are adapted to be in an on state in which the reminder is issued and an off state in which the reminder is not issued. The reminder control is adapted to allow a user to change the first setting between the on state and the off state. The arming control is adapted to arm and disarm the monitoring system. The controller is configured to detect when a patient is present on the support surface and to display the reminder on the display if the first setting is in the on state and the monitoring system is not armed. The controller is further adapted to not display the reminder on the display if the second setting is in the off state.

According to another aspect of the present disclosure, when both the first and second settings are in the off state, the controller is adapted not to display the reminder. When both the first and second settings are in the on state, the controller is adapted to display the reminder. The controller is further adapted to display the reminder if the first setting is in the off state and the second setting is in the on state, and to not display the reminder if the first setting is in the on state and the second setting is in the off state. The user is able to turn the second setting on and off for a given patient.

In some aspects, the reminder includes a first option to dismiss the reminder and a second option to turn off the reminder. The controller is adapted to remove the reminder when a user selects the first option, but to leave the first and second settings unchanged. When a user selects the second option, the controller is adapted to remove the reminder and set the second setting to the off state.

In some aspects, the arming control automatically switches the second setting to the on state when the monitoring system is armed.

In some aspects, the reminder control automatically switches the second setting to the off state when the first setting is set to the off state.

In some aspects, the patient support apparatus includes a new patient control. When activated, the new patient control is configured to leave the first setting unchanged and automatically change the second setting to the same state as the first setting. The new patient control may also erase patient-specific data stored in memory when the new patient control is activated.

According to one aspect of the present invention, the patient support apparatus further includes an audio playback circuit in communication with the controller. The audio playback circuit stores at least one audio file used to alert hospital staff if the monitoring system is armed and is triggered. An amplifier is in communication with the audio playback circuit and the amplifier increases the volume of the audio file. The amplifier is connected to a speaker which emits the audio file to alert a caregiver that the monitoring system has been triggered.

Before the various aspects disclosed herein are explained in detail, it is to be understood that the claims are not to be limited to the details of operation, to the details of construction, or to the arrangement of the components set forth in the following description or illustrated in the drawings. The aspects described herein are capable of being practiced or being carried out in alternative ways not expressly disclosed herein. In addition, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various aspects. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 9 is an illustrative bed exit reminder screen that may be displayed on the display of the first user interface;

FIG. 10 is an illustrative monitoring system reminder screen that may be displayed on the display of the first user interface;

FIG. 11 is an illustrative global settings screen that may be displayed on the display of the first user interface;

DETAILED DESCRIPTION OF THE EMBODIMENTS

Figure 1:
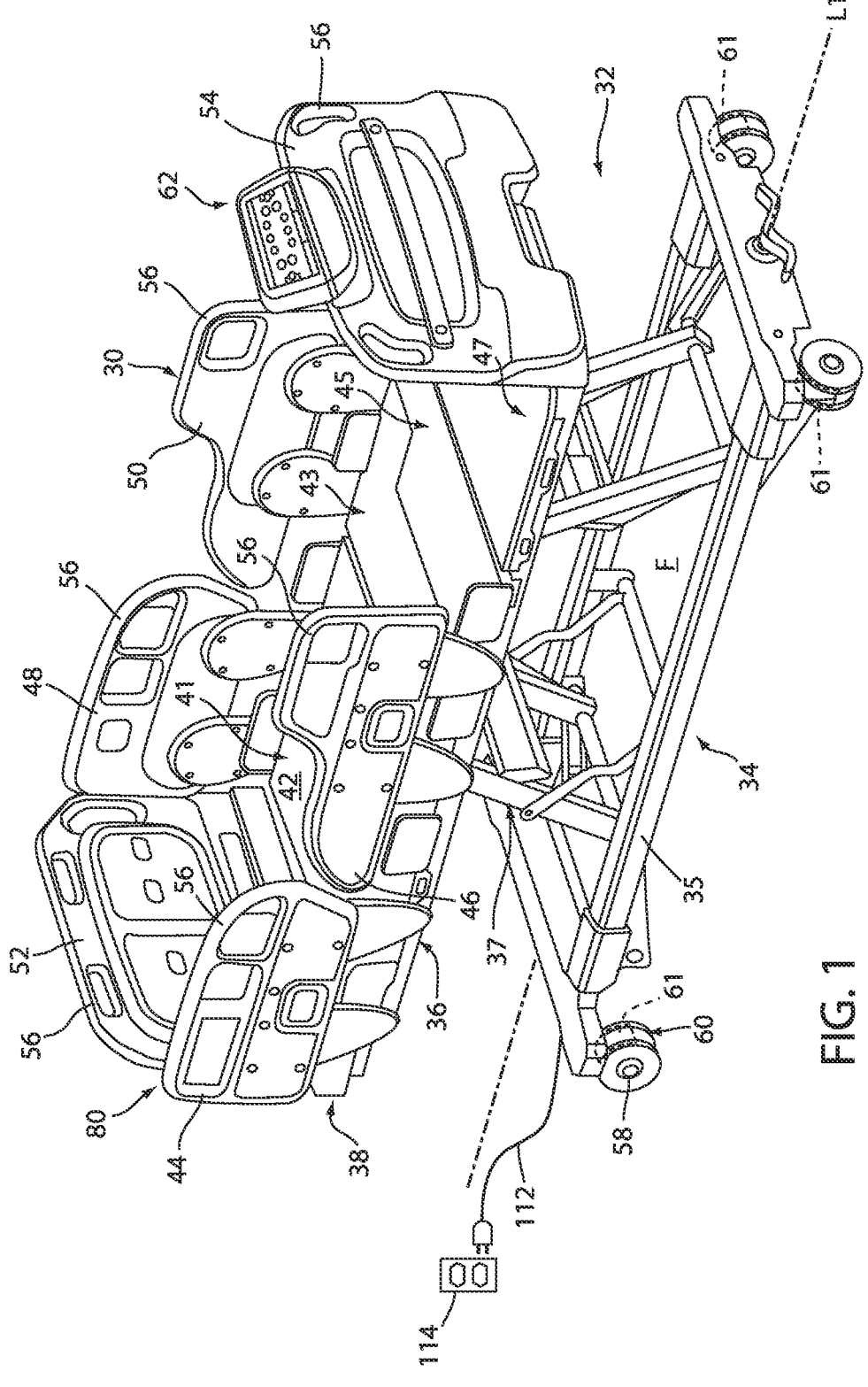
FIG. 1 is a perspective view of a patient support apparatus having first and second user interfaces, according to one aspect of the disclosure.

An illustrative patient support apparatus 30 incorporating one or more aspects of the present disclosure is shown in FIG. 1. Such a patient support apparatus may be like that described in WIPO PCT Application No. 2002/257475, filed on Jun. 18, 2020, entitled "Patient Support Apparatus With Caregiver Reminders," the complete disclosure of which is hereby incorporated herein by reference. Although the particular form of patient support apparatus 30 illustrated in FIG. 1 is a bed adapted for use in a hospital or other medical setting, it will be understood that patient support apparatus 30 could, in different aspects, be a cot, a stretcher, a gurney, a recliner, an operating table, a residential bed, or any other structure capable of supporting a person, whether stationary or mobile and/or whether medical or residential.

A support structure 32 provides support for the patient. The support structure 32 illustrated in FIG. 1 comprises a base 34 and a support frame 36. The base 34 comprises a base frame 35. The support frame 36 is spaced above the base frame 35 in FIG. 1. The support structure 32 also comprises a patient support deck 38 disposed on the support frame 36. The patient support deck 38 comprises several sections, some of which are capable of articulating (e.g., pivoting) relative to the support frame 36, such as a back (fowler) section 41, a seat section 43, a leg section 45 and a foot section 47. The patient support deck 38 provides a patient support surface 42 upon which the patient is supported. A lift system 37 may be coupled to the support structure 32 to raise and lower the support frame 36, patient support deck 38, and patient support surface 42 to different heights relative to the base frame 35, including to a lowest height relative to the base frame 35. Such a lift system 37 may be like that described in U.S. Patent Application Pub. No. 2017/0246065, filed on Feb. 22, 2017, entitled "Lift Assembly For Patient Support Apparatus," the complete disclosure of which is hereby incorporated herein by reference.

A mattress (not shown) is disposed on the patient support deck 38 during use. The mattress comprises a secondary patient support surface upon which the patient is supported. The base 34, support frame 36, patient support deck 38, and patient support surface 42 each have a head end and a foot end corresponding to designated placement of the patient's head and feet on patient support apparatus 30. The base 34 comprises a longitudinal axis L1 along its length from the head end to the foot end. The construction of the support structure 32 may take on any known or conventional design, and is not limited to that specifically set forth above.

Patient barriers, such as side rails 44, 46, 48, 50 are coupled to the support frame 36 and/or patient support deck 38 and are thereby supported by the base 34. A first side rail 44 is positioned at a right head end. A second side rail 46 is positioned at a right foot end. A third side rail 48 is positioned at a left head end. A fourth side rail 50 is positioned at a left foot end. In the aspect shown, the head end side rails 44, 48 are mounted to the back section 41 for movement with the back section 41. The foot end side rails 46, 50 are mounted to the support frame 36 for movement with the support frame 36. If patient support apparatus 30 is a stretcher or a cot, there may be fewer side rails. The side rails 44, 46, 48, 50 are movable relative to the back section 41/support frame 36 to a raised position in which the side rails 44, 46, 48, 50 block ingress and egress into and out of patient support apparatus 30, one or more intermediate positions, and a lowered position in which the side rails 44, 46, 48, 50 are not an obstacle to such ingress and egress. In the aspect shown, the side rails 44, 46, 48, 50 are connected to the back section 41 and/or the support frame 36 by pivotal support arms to form four bar linkages. Such side rails and the manner in which they may be raised/lowered are shown and described in U.S. Patent Application Pub. No. 2017/0172829, filed on Dec. 15, 2016 and entitled "Powered Side Rail For A Patient Support Apparatus," the complete disclosure of which is hereby incorporated herein by reference.

A headboard 52 and a footboard 54 are coupled to the support frame 36. The headboard 52 and footboard 54 may be coupled to any location on patient support apparatus 30, such as the support frame 36 or the base 34. In still other aspects, patient support apparatus 30 does not include the headboard 52 and/or the footboard 54.

Caregiver interfaces 56, such as handles, are shown integrated into the headboard 52, footboard 54, and side rails 44, 46, 48, 50 to facilitate movement of patient support apparatus 30 over a floor surface F. Additional caregiver interfaces 56 may be integrated into other components of patient support apparatus 30. The caregiver interfaces 56 are graspable by the caregiver to manipulate patient support apparatus 30 for movement, to move the side rails 44, 46, 48, 50, and the like.

Wheels 58 are coupled to the base 34 to facilitate transport over the floor surface F. The wheels 58 are arranged in each of four quadrants of the base 34 adjacent to corners of the base 34. In the aspect shown, the wheels 58 are caster wheels able to rotate and swivel relative to the support structure 32 during transport. Each of the wheels 58 forms part of a caster assembly 60. Each caster assembly 60 is mounted to the base 34. Brake 61 may be associated with one or more of the wheels 58 to arrest rotation of the wheels when active. Brake 61 may be manually or electronically actuated. It should be understood that various configurations of the caster assemblies 60 and/or brake 61 are contemplated. In addition, in some aspects, the wheels 58 are not caster wheels and may be non-steerable, steerable, non-powered, powered, or combinations thereof. Additional wheels are also contemplated. For example, patient support apparatus 30 may comprise four non-powered, non-steerable wheels, along with one or more powered wheels. In some cases, patient support apparatus 30 may not include any wheels.

In other aspects, one or more auxiliary wheels (powered or non-powered), which are movable between stowed positions and deployed positions, may be coupled to the support structure 32. In some cases, when these auxiliary wheels are located between caster assemblies 60 and contact the floor surface F in the deployed position, the auxiliary wheels cause two of the caster assemblies 60 to be lifted off the floor surface F, thereby shortening a wheel base of patient support apparatus 30. A fifth wheel may also be arranged substantially in a center of the base 34.

The mechanical construction of patient support apparatus 30 may be the same as, or nearly the same as, the mechanical construction of the Model 3002 S3 bed manufactured and sold by Stryker Corporation of Kalamazoo, Michigan. This mechanical construction is described in detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 30 can be designed with other types of mechanical constructions, such as, but not limited to, those described in U.S. Pat. No. 7,690,059, issued Apr. 6, 2010, entitled "Hospital Bed," and/or U.S. Pat. No. 8,689,376, issued Apr. 8, 2014, entitled "Patient Handling Device Including Local Status Indication, One-Touch Fowler Angle Adjustment, and Power-On Alarm Configuration", the complete disclosures of both of which are hereby incorporated herein by reference. The mechanical construction of patient support apparatus 30 may also take on forms different from what is disclosed in the aforementioned references.

Additionally, patient support apparatus 30 includes a user interface 62 supported by the support structure 32 of patient support apparatus 30. Although shown at the foot end of patient support apparatus 30, user interface 62 may be disposed at the head end, and/or on one or more sides of patient support apparatus 30. More specifically, one or more user interfaces 62 may be attached to the headboard 52, footboard 54, and/or side rails 44, 46, 48, 50, or at any other suitable location, via fasteners, welding, snap-fit connections, or the like. In some versions, each user interface 62 comprises a separate housing fixed to the headboard 52, footboard 54, and/or side rails 44, 46, 48, 50, or other suitable locations. In other versions, the housings of user interfaces 62 are integrated into the headboard 52, footboard 54, and/or side rails 44, 46, 48, 50. In at least one aspect, one of the user interfaces 62 is attached to the footboard 54 of patient support apparatus 30 and other user interfaces 62 are attached to one or more of the side rails 44, 46, 48, 50. A user interface 62 attached to the footboard 54 shall be described in detail, but the features and functions to be described are equally applicable to the other user interfaces 62 that may be located elsewhere on patient support apparatus 30.

Figure 2:
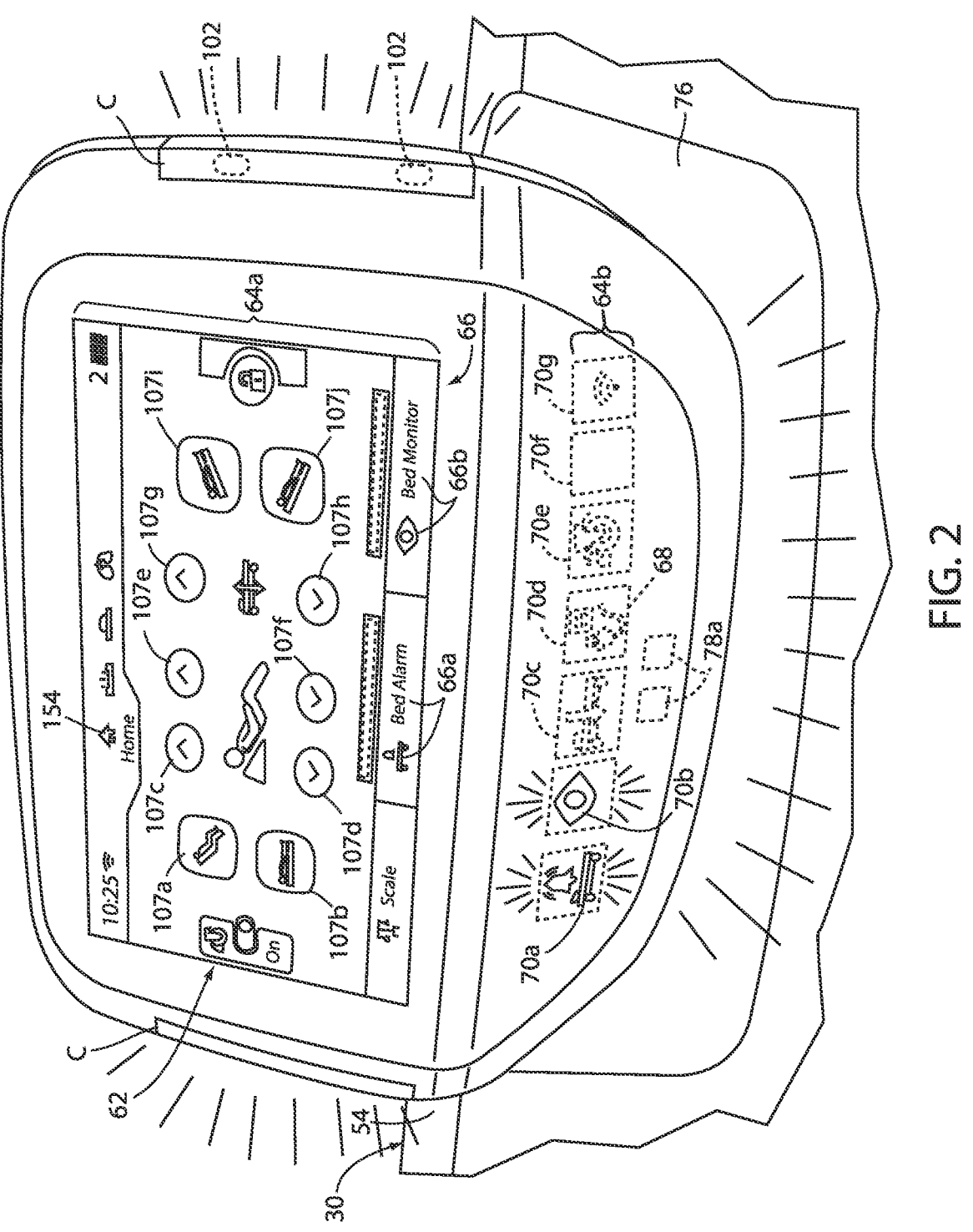
FIG. 2 is a partial perspective view of the first user interface depicted in FIG. 1.

FIG. 2 depicts a perspective view of user interface 62 attached to the footboard 54. User interface 62 includes a display 64a. Display 64a may be a touchscreen-type display, although it will be understood that a non-touchscreen display may alternatively be used. Display 64a displays one or more visual indicators, one or more controls, and/or one or more control screens, as will be discussed more below. Display 64a may comprise an LED display, OLED display, or another type of display.

Display 64a is configured to display a plurality of different screens thereon, only one of which is shown in FIG. 2. Specifically, display 64a is shown in FIG. 2 displaying a motion control screen 154. Motion control screen 154 includes a plurality of motion controls 107a-i that, when touched, cause movement of the associated component(s) of patient support apparatus 20. Thus, for example, pressing and holding motion control 107c causes back section 41 to be pivoted upwardly, while pressing and holding motion control 107d causes back section 41 to be pivoted downwardly. If the user wishes to control other aspects of patient support apparatus 20 besides movement, he or she can navigate to different screens that include different controls and/or other information about patient support apparatus. Thus, for example, if the user presses navigation control 66a, user interface 62 displays an exit detection control screen 300 (shown in FIG. 14) that allows the user to control various aspects of exit detection system 150. If the user presses navigation control 66b, user interface 62 displays a monitoring control screen 350 (shown in FIG. 17) that allows the user to control various aspects of the monitoring system 152. If the user presses navigation control 66c, user interface 62 displays a scale screen (not shown) that allows the user to take a patient weight reading and/or control other aspects of the scale system. Still further, if the user presses home navigation control 66d, user interface 62 displays a home screen that, in some aspects, includes controls for accessing all of the functionality of patient support apparatus 20.

In some aspects, if the user presses navigation control 66a, patient support apparatus 30 is configured to not only display the exit detection control screen 300, but to also automatically arm exit detection system 150. In such aspects, patient support apparatus 30 may also be configured to both display a monitoring screen and to automatically arm monitoring system 152 in response to the user touching navigation control 66b. Further details of the operation of these navigation controls 66a and 66b, in at least one aspect, are disclosed in commonly assigned U.S. patent application Ser. No. 62/868,240, filed Jun. 28, 2019, by inventors Kurosh Nahavandi et al. and entitled "Patient Support Apparatus with Improved User Interface," the complete disclosure of which is incorporated herein by reference.

User interface 62, in some aspects, also includes a dashboard 64b (FIG. 2) that communicates the current states of various conditions of patient support apparatus 30 to a caregiver. Dashboard 64b comprises a plurality of icons 70 that are illuminated via icon lights 68 to thereby act as visual indicators for indicating the current state of different conditions of patient support apparatus 30. For example, a first icon 70a (e.g., a graphical symbol of an alert over a bed) is backlit by a corresponding light 68 when exit detection system 150 is armed; a second icon 70b (e.g., a graphical symbol of an eye) is backlit by a second light 68 when monitoring system 152 is armed; a third icon 70c (e.g., a graphical symbol of an arrow and bed) is backlit by a third light 68 when the bed is at its lowest height (or below a threshold height); a fourth icon 70d (e.g., a graphical symbol of an unplugged AC power cord) is backlit by a fourth light 68 when the patient support apparatus 20 is plugged into an electrical wall outlet; and a fifth icon 70e (e.g., a graphical symbol of a lock and wheel) is backlit by a fifth light 68 when the brake is activated. The lights 68 positioned behind these icons 70a-e may be controlled to be illuminated in different colors, depending upon what state the associated condition is currently in (e.g. the brake is deactivated, exit detection system 150 is disarmed, etc.) and/or one or more of them may alternatively not be illuminated at all when the associated condition is in another state. Fewer or additional icons 70 may be included as part of dashboard 64b. The plurality of icons 70 may be dead-fronted on the dashboard 64b of user interface 62 such that the plurality of icons 70 are only visible by the caregiver when illuminated by icon lights 68 supported in the housing of user interface 62.

Dashboard 64b, unlike display 64a, retains the illumination of one or more of icons 70a-e at all times. That is, display 64a is configured in some aspects to go to sleep (blank) after a predetermined time period elapses without usage. Dashboard 64b, however, retains the illumination of the various icons 70 even after display 64a goes blank, thereby providing the caregiver with information about the status of patient support apparatus 30 when display 64a is blank. Thus, for example, if the brake is not activated and icon 70e is illuminated with an amber or red color, this illumination remains for as long as the brake remains inactive, even if display 64a times out and goes to sleep (or otherwise goes blank).

Still referring to FIG. 2, one or more reflective surfaces 76 may be located on the patient support apparatus 30 proximate user interface 62. The reflective surfaces 76 may be disposed relative to user interface 62 such that one or more indirect lights 78a supported by the housing of user interface 62 project light away from user interface 62 toward the reflective surfaces 76 to be reflected off the reflective surfaces 76 and outward from the patient support apparatus 30 to act as another visual indicator. Indirect lights 78a may be located on a bottom of the housing of user interface 62 to project the light away from the bottom of the housing toward the reflective surfaces 76. Accordingly, indirect lights 78a may be hidden from view by the housing. The light may be reflected, for example, in several directions, including generally horizontal directions, for being easily viewed by a caregiver at a distance from the patient support apparatus 30. As shown in FIG. 2, in one example, one of the reflective surfaces 76 is disposed underneath user interface 62 to reflect light away from the patient support apparatus 30. The reflective surface 76 may be a surface of the footboard 54, or may be any surface capable of reflecting light from indirect lights 78a, and may be present elsewhere on the patient support apparatus 30. Similar reflective surfaces 76 may be present on the headboard 52 and/or one or more of the side rails 44, 46, 48, 50 to reflect light from other user interfaces 62.

Reflective surfaces 76 are adapted in many aspects to generate diffuse reflection, rather than specular reflection. That is, surfaces 76 are not mirrored surfaces, but instead are colored surfaces that scatter the light emitted from lights 78a in multiple directions and/or at many angles. In many aspects, surfaces 76 are colored a white color, or an off-white color, such that the color composition of the light emitted by indirect lights 78a is not substantially changed after reflection from surfaces 76. The color of light emitted by indirect lights 78a is variable, and in several aspects, comprises the same color palette as icon lights 68. For example, in at least one aspect, indirect lights 78a may emit light of three different colors: amber, red, and green, and icon lights 68 are also able to emit light of the same three colors. It will be understood that the term "light" as used herein is broad enough to cover multiple LEDs, bulbs, or other light emitting structures, such that the term "light" includes structures wherein one LED, bulb, or the like is used for emitting a first color, a second LED, bulb, or the like is used for emitting a second color, and so on.

Indirect lights 78a are configured to emit light constantly at certain times, to emit light in a pulsed fashion at other times, and to emit light in a flashing fashion at still other times. The times at which first and second lights are configured to be controlled in this manner, as well as the colors of the light that they are adapted to emit, are discussed in greater detail below.

Both icon lights 68 and indirect lights 78 may comprise RGB LEDs ("Red-Green-Blue Light Emitting Diodes"). Icon lights 68 and/or indirect lights 78 may comprise a single RGB LED, or may comprise a plurality of LEDs. Icon lights 68 and indirect lights 78 may also comprise one or more incandescent bulbs, halogen lamps, neon lamps, fluorescent tubes, and/or any other types of light emitting devices. In some aspects, patient support apparatus 20 includes one or more direct lights 102 located on the sides of user interface 62 that emit light through light-transmitting covers C attached to the housing of user interface 62 (FIG. 2). When included, direct lights 102 are controlled in synchrony with indirect lights 78a, as will be discussed in greater detail below.

Figure 3:
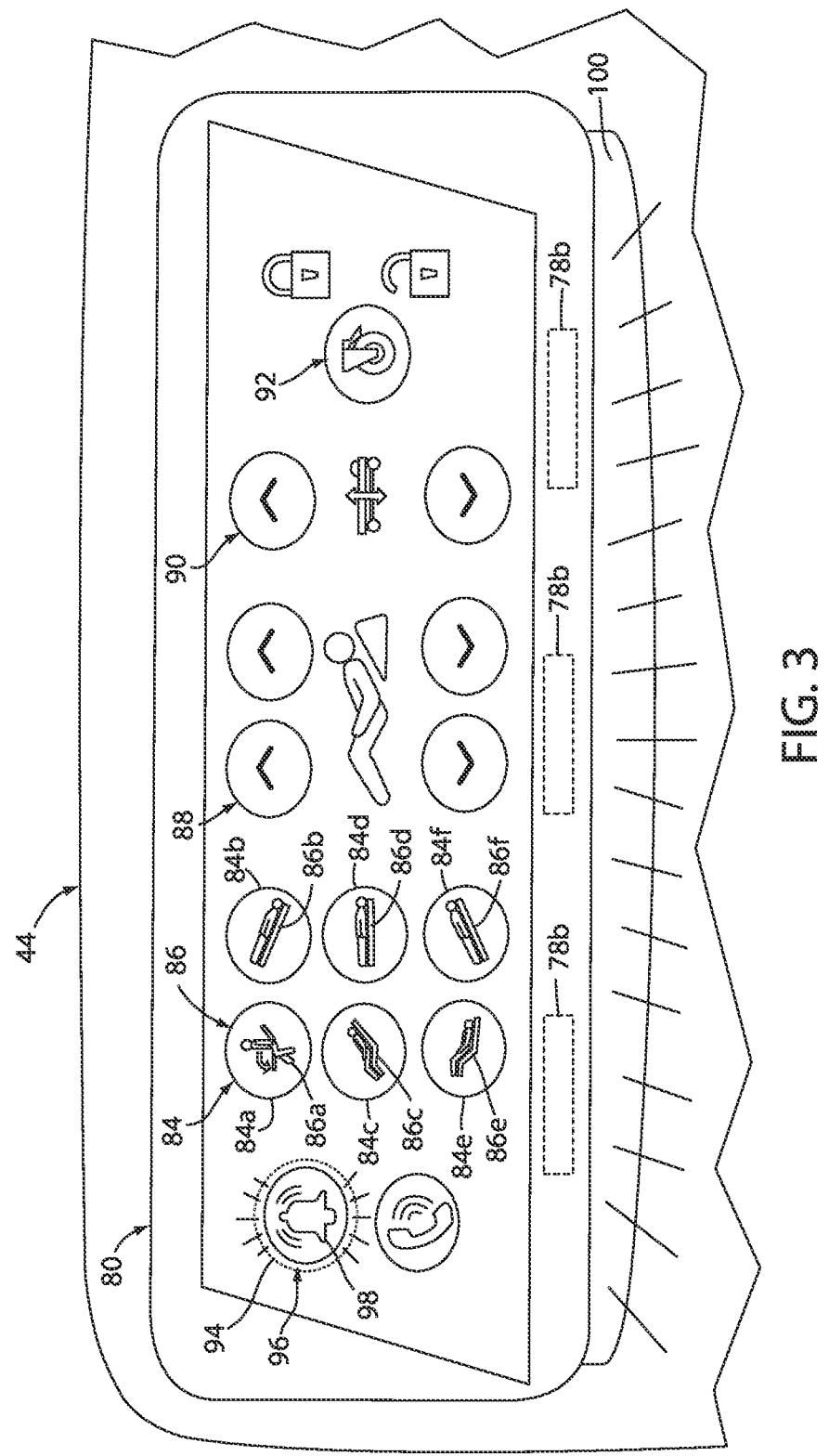
FIG. 3 is a partial perspective view of the second user interface depicted in FIG. 1.

In some aspects, additional user interfaces may be present on the patient support apparatus 30, spaced from user interface 62. FIG. 3 depicts a perspective view of a user interface 80 attached to the side rail 44. A similar user interface 80 may be located on an opposing side rail. These user interfaces 80 may have more or less functionality than user interface 62, and may have their own displays, indicator panels with associated icons, and/or reflective surfaces to project light outward from the side rails, for example.

User interface 80 includes a plurality of controls and one or more visual indicators. The controls include bed orientation controls 84 with associated icons 86; support deck section controls 88 which raise and lower the back (fowler) section 41 and leg section 45 of the patient support deck 38 relative to the support frame 36; bed height controls 90 which operate the lift system 37 to raise and lower the support frame 36, patient support deck 38, and patient support surface 42 to different heights relative to the base frame 35; and brake control 92 which operates brake 61 (e.g. turns brake 61 on and off)

As shown in FIG. 3, in one aspect, the plurality of bed orientation controls 84 includes an egress control 84a which is represented on the interface by a first icon 86a (e.g., an associated graphical symbol of a patient leaving a bed). Egress control 84a is a user input device associated with facilitating egress of the patient from the patient support apparatus 30. Pressing egress control 84a reconfigures the patient support apparatus 30 into a position that allows easier exit from the apparatus or an "egress orientation." The same control 84a, or a similar control (not shown), can be employed to allow ingress into the patient support apparatus 30.

Other bed orientation controls include a Trendelenburg control 84b for reconfiguring the patient support apparatus 30 into a Trendelenburg orientation, which is represented on the interface by a second icon 86b (e.g. an associated graphical symbol of a patient in a Trendelenburg position), a chair control 84c for reconfiguring the patient support apparatus 30 into a chair orientation, which is represented on the interface by a third icon 86c (e.g. an associated graphical symbol of a patient in a chair position), a flat control 84d for reconfiguring the patient support apparatus 30 into a flat orientation, which is represented on the interface by a fourth icon 86d (e.g. an associated graphical symbol of a patient in a supine position), a foot elevation control 84e for reconfiguring the patient support apparatus 30 into a foot elevation orientation, which is represented on the interface by a fifth icon 86e (e.g. an associated graphical symbol of a patient in a foot elevation position), and a reverse Trendelenburg control 84f for reconfiguring the patient support apparatus 30 into a reverse Trendelenburg orientation, which is represented on the interface by a sixth icon 86f (e.g. an associated graphical symbol of a patient in a reverse Trendelenburg position).

User interface 80 includes a reminder light 94 that is activated in order to remind the caregiver to disarm exit detection system 150 prior to the patient egressing from the apparatus 30. An arming/disarming control 96 is provided, in some aspects, on user interface 80 to allow the caregiver to arm or disarm exit detection system 150 from the user interface 80. As shown in FIG. 3, in one aspect, the reminder light 94 is supported in the housing of user interface 80 that illuminates an associated icon 98 (e.g., a graphical symbol of an alert) of the arming/disarming control 96.

In at least one aspect, reminder light 94 is controlled to emit white light (steady, flashing, or pulsing) when a user presses on egress control 84a while exit detection system 150 is armed, and to emit no light at all other times except when exit detection system 150 is armed and detects a patient exiting from patient support apparatus 30. When such a patient exit is detected, reminder light 94 may be activated to emit a red flashing light. The red flashing illumination of reminder light 94 during an exit detection alert is configured, in at least some aspects, to be synchronized with the red flashing of other lights (e.g. indirect lights 78a, 78b) that also occurs when an exit detection alert is issued. Such synchronization means that not only is reminder light 94 activated at the same times as the other lights, but the waveform used to carry out the flashing (non-sinusoidal) is of the same period, frequency, and general shape (although the amplitude may be different). Other manners of activating reminder light 94 may also be employed.

Icon 98 is positioned over reminder light 94 such that reminder light 94 illuminates icon 98 when reminder light 94 is activated. The illumination of icon 98 serves to remind the caregiver to disarm exit detection system 150 when egress control 84*a* is pressed and exit detection system 150 is armed. Further, the flashing illumination of icon 98 by reminder light 94 during a bed exit alert serves as an additional indication to the caregiver of the cause of the alert. In the illustrated aspect, icon 98 and reminder light 94 are integrated into an arming/disarming control 96. Arming/disarming control 96 enables the caregiver to disarm and/or arm exit detection system 150 when pressed. In some aspects, reminder light 94 may be separate and spaced from arming/disarming control 96 and/or user interface 80 may omit arming/disarming control 96.

Still referring to FIG. 3, at least one reflective surface 100 is located on the side rails proximate user interface 80. The reflective surface 100 is disposed relative to user interface 80 such that one or more indirect lights 78*b* supported by the housing of user interface 80 project light away from user interface 80 toward the reflective surface 100 to be reflected off the reflective surface 100 and outward from the side rails to act as another visual indicator.

Indirect lights 78*b* are located on a bottom of the housing of user interface 80 and project light away from the bottom of the housing toward the reflective surface 100. Accordingly, indirect lights 78*b* are hidden from view by the housing. The light they emit is reflected, for example, in several directions, including generally horizontal directions, for being easily viewed by a caregiver at a distance from the patient support apparatus 30. As shown in FIG. 3, in one example, one of the reflective surfaces 100 is disposed underneath user interface 80 to reflect light away from the side rail 44. Reflective surface 100, like reflective surface 76, is a diffuse reflector, not a specular reflector, and is, in at least some aspects, the same color as reflective surface 76.

As will be discussed in more detail below, icon lights 68, indirect lights 78*a-b*, and direct lights 102 are controlled to emit lights in different manners at different times, depending upon the state of patient support apparatus 30. Specifically, icon lights 68, indirect lights 78*a-b*, and direct lights 102 may be activated continuously at times, may be flashed at other times, and may be pulsed at still other times. As used herein, the term "pulsing" or its variants refers to controlling the illumination of one or more lights such that its light intensity increases and decreases in a generally sinusoidal manner. That is, the light gradually gets brighter and brighter until it reaches a peak and then gradually gets dimmer and dimmer until it reaches a trough (which may have the light completely shut off for a fleeting moment), and then this cycle repeats. In contrast, the term "flashing" refers to changing the intensity of the lights, but in a manner that is much more precipitous. For example, in some aspects, "flashing" refers to controlling the lights such that the intensity of the light they emit generally varies in a square wave fashion. Alternatively, flashing of the lights may be carried out such that the emitted light intensity varies generally as a sawtooth wave, or as a triangle wave, or in some other non-sinusoidal manner. By using a non-sinusoidal wave form for flashing the lights, the effect is to present a visually harsher and more immediate sense of urgency to the caregiver than the sinusoidal waveform used during the pulsing of the lights. For this reason, lights 68 and/or 78 are pulsed as part of a gentle reminder to the caregiver and flashed when an alert is issued, as will be discussed in greater detail below.

The flashing of the lights may also be carried out at a higher frequency than the pulsing of the lights. In at least one aspect, the pulsing of lights 68, 78*a-b*, 102 repeats itself with a frequency on the order of once every two to five seconds, although other frequencies may be used. By pulsing at this frequency, the synchronized illumination of lights 68, 78*a-b*, and 102 changes its intensity with roughly the same frequency as a human breathes, and this relatively low time period creates a non-urgent, yet persistent, visual effect, thereby reminding the caregiver that one or more tasks still need to be completed to put patient support apparatus 30 in the proper configuration, yet doing so in a manner that is not distractive or unappealing to the caregiver. In contrast, the synchronized flashing of lights 68, 78*a-b*, and 102 is carried out, in at least one aspect, at a frequency faster than once every two to five seconds, such as, but not limited, to, at least once per second, if not faster. As will be discussed more below, the flashing of lights is typically only implemented when an alert has issued (red flashing when exit detection system 150 detects a patient alert; amber flashing when monitoring system 152 detects an alert with respect to a monitored condition), while the pulsing of the lights (amber) is typically only implemented when a reminder is being communicated to the caregiver to perform one or more configuration tasks with respect to patient support apparatus 30.

Figure 4:
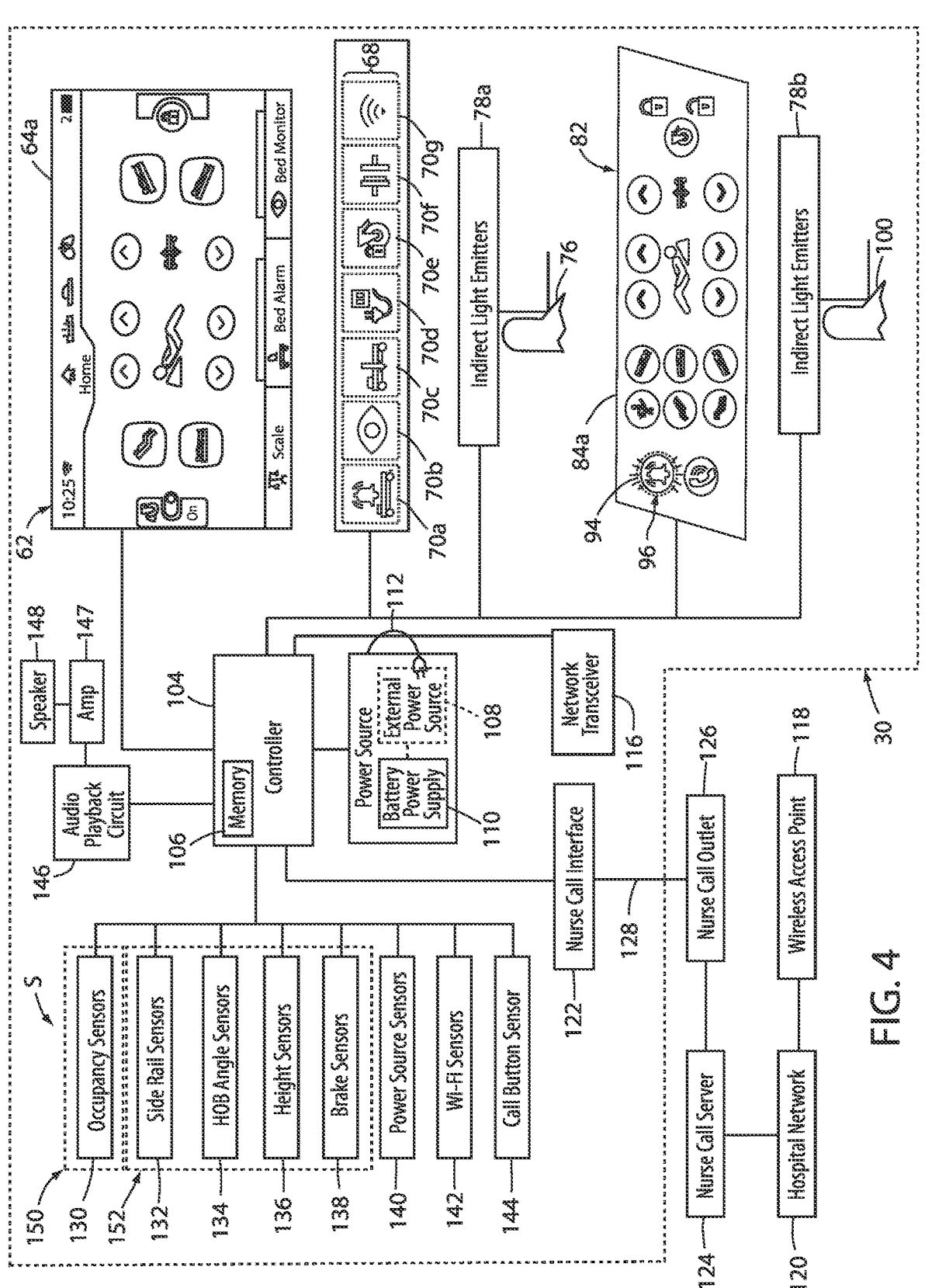
FIG. 4 is a schematic diagram of various components of the patient support apparatus and its environment, including the first user interface and a sensor system.

FIG. 4 illustrates various components of user interface 62 in more detail, as well as a sensor system S coupled to user interface 62 and several other components of patient support apparatus 20 that interact with user interface 62. User interface 62 includes a controller 104 having one or more microprocessors, microcontrollers, field programmable gate arrays, systems on a chip, discrete circuitry, and/or other suitable hardware, software, or firmware that is capable of carrying out the functions described herein. Controller 104 is adapted to communicate with side rail user interfaces 80 via a network bus (e.g. a Controller Area Network, a Serial Peripheral Interface (SPI) bus, an Ethernet connection, a RS-485 bus, etc.). Controller 104 sends commands and messages to one or more control structures within user interface 80 that carry out the selective activation and deactivation of indirect lights 78*b* and/or reminder lights 94. As will be discussed more below, the activation of indirect lights 78*b* is typically carried out in synchrony with indirect lights 78*a*, direct lights 102, and, in at least some situations, icon lights 68. Controller 104 is configured to process instructions stored in memory 106 to control operation of user interface 62 and lights 68, 78*a-b*, 94, and 102. Controller 104 also controls what screens are shown on display 64*a*.

Power to the patient support apparatus 30 is provided by an external power source 108 or a battery power supply 110. An alternating current (A/C) power cord 112 provides power from the external power source 108 to the patient support apparatus 30 and is plugged into a corresponding outlet (e.g., wall outlet 114, FIG. 1) to receive external power.

Patient support apparatus 30 includes a wireless network transceiver 116 (FIG. 4), such as, but not limited to, a Wi-Fi transceiver 116 adapted to wirelessly communicate with one or more wireless access points 118 of a conventional healthcare facility network 120. The wireless access points 118 are adapted to communicate with a hospital network 120 (e.g. a local area network or LAN) of the facility in which the patient support apparatus 30 is located. Controller 104 is thereby able to use network transceiver 116 to send signals to and receive signals from one or more servers located on hospital network 120.

Patient support apparatus 30 also includes a nurse call interface 122 for communicatively coupling patient support apparatus 30 to a conventional nurse call system. Conventional nurse call systems typically include one or more nurse call servers 124 coupled to the hospital network 120, one or more nurse call outlets 126 positioned in each patient room, wiring coupling the nurse call outlets 126 to nurse call server 124, and other structures. In some aspects, nurse call interface 122 is a wired interface adapted to couple to, and communicate with, nurse call outlet 126 via a nurse call cable 128. A first end of cable 128 is coupled to nurse call interface 122 and the other end is coupled to nurse call outlet 126. One example of such a wired nurse call interface is the cable interface disclosed in more detail in commonly assigned U.S. Patent Application Publication No. 2018/ 0293849, filed on Apr. 4, 2018 and entitled "Patient Support Apparatuses with Reconfigurable Communication," the complete disclosure of which is incorporated herein by reference.

In other aspects, nurse call interface 122 is a wireless interface adapted to communicate wirelessly with nurse call outlet 126. Several examples of wireless nurse call interfaces 122 that enable wireless communication between patient support apparatus 30 and an adjacent nurse call outlet 126 are disclosed in the following commonly assigned patent references and may be implemented in patient support apparatus 30 herein: U.S. Patent Application Publication No. 2016/0038361, filed on Aug. 6, 2015 and entitled "Patient Support Apparatuses with Wireless Headwall Communication"; U.S. patent application Ser. No. 16/217,203, filed on Dec. 12, 2018 and entitled "Smart Hospital Headwall System"; U.S. patent application Ser. No. 16/193,150, filed on Nov. 16, 2018 and entitled "Patient Support Apparatuses with Location/Movement Detection"; and U.S. patent application Ser. No. 16/215,911, filed on Dec. 11, 2018 and entitled "Hospital Headwall Communication System," the complete disclosures of all of which are incorporated herein by reference. Still other types of wireless or wired nurse call interfaces may, of course, be used.

A sensor system S comprising one or more sensors 130, 132, 134, 136, 138, 140, 142, 144 is integrated into the patient support apparatus 30 to generate one or more signals corresponding to the various states of the monitored conditions. Controller 104 issues commands to user interfaces 62, 80 and the lights 68, 78a-b, 94, 102 based on the signals that controller 104 receives from sensor system S. Thus, sensor system S provides inputs to controller 104 of the various states of different components of patient support apparatus 30 and controller 104 uses that state data to output commands to user interfaces 62, 80, and/or the lights 68, 78a-b, 94, 102.

Sensor system S includes one or more force sensors 130, side rail sensors 132, HOB angle sensors 134, height sensors 136, brake sensors 138, power source sensors 140, WiFi connections sensors 142, and nurse call connection sensors 144. Force sensors 130 output signals in response to downward forces exerted onto support deck 38 by the patient and/or objects, and force sensors 130 may be implemented as load cells, although other types of force sensors may be used. Side rail sensors 132 output signals that indicate a current position of side rails 44, 46, 48, 50 so that controller 104 can determine whether the side rails 44, 46, 48, 50 are in the raised position (up), lowered position (down), or in one of the intermediate positions.

HOB angle sensor 134 outputs signals that indicate a current angle of the back section 41 so that controller 104 can determine whether the back section 41 is at or above a preset angle relative to the support frame 36 or at less than the preset angle. Height sensors 136 output signals that indicate a current height of the support frame 36 so that controller 104 can determine whether patient support apparatus 30 is at the lowest height or not. Brake sensors 138 output signals that indicate whether the brakes 61 are active (on) or inactive (off). Power source sensors 140 output signals that indicate whether or not the AC power plug that provides power from the external power source 108 to patient support apparatus 30 is plugged into a corresponding outlet (e.g., wall outlet) to receive external power. The Wi-Fi connection sensors 142 output signals that indicate whether the Wi-Fi transceiver 116 is connected or disconnected to the wireless access point 118 (or a specific server on network 120). Nurse call sensor 144 outputs signals that indicate whether the nurse call interface 122 is connected to the nurse call outlet 126 or disconnected from the nurse call outlet 126.

These sensors 130, 132, 134, 136, 138, 140, 142 may include one or more load cells, pressure sensors such as piezoelectric and piezoresistive sensors, Hall Effect sensors, capacitive sensors, resonant sensors, thermal sensors, limit switches, gyroscopes, accelerometers, motion sensors, ultrasonic sensors, range sensors, potentiometers, magnetostrictive sensors, electrical current sensors, voltage detectors, and/or any other suitable types of sensors for carrying out their associated functions.

Force sensors 130 are part of an exit detection system 150 that determines if the occupant has exited patient support apparatus 30. Force sensors 130 can also be part of a scale system that detects the weight of an occupant of patient support apparatus 30, the details of which are not described herein. Force sensors 130 are adapted to detect downward forces exerted on the patient support surface 42, i.e. by an occupant of support deck 38. Thus, when an occupant is positioned on support deck 38 and substantially still (i.e. not moving in a manner involving accelerations that cause forces to be exerted against support deck 38), force sensors 130 will detect the weight of the occupant. Force sensors 130 can also be used to determine a center of gravity of the occupant in order to determine if the occupant is about to exit patient support apparatus 30. In alternative aspects, the outputs from force sensors 130 are analyzed, not to determine a center of gravity, but instead to determine a weight distribution and/or a change in weight distribution, such as by determining one or more ratios of the relative weights sensed by force sensors 130 and using them to determine if the occupant is about to exit patient support apparatus 30. In still other aspects, force sensors 130 may be modified to detect forces other than, or in addition to, the downward forces exerted by the occupant. Other types of sensors may additionally or alternatively be used for determining if the patient has exited, or is about to exit.

The particular structural details of exit detection system 150 can vary widely. In some aspects, exit detection system 150 is constructed in accordance with the exit detection system described in U.S. Pat. No. 5,276,432, issued Jan. 4, 1994, entitled "Patient Exit Detection Mechanism for Hospital Bed," the complete disclosure of which is hereby incorporated herein by reference. In such aspects, exit detection system 150 may include multiple zones that trigger an alert when the patient's center of gravity travels outside of the zone. In this manner, exit detection system is able to have its sensitivity selected by the caregiver. Other types of exit detection systems may also or alternatively be used.

Exit detection system 150 is configured to be armed and disarmed. When armed, exit detection system 150 issues an alert when the occupant exits patient support surface 42, or is about to exit patient support apparatus 30. In response to the alert issued by exit detection system 150, controller 104 flashes lights 68, 78a-b, and 102 (and in some cases, reminder light 94) in a red color. Controller 104 may also display an exit detection alert screen on display 64a which includes portions that are red and that flash in synchrony with lights 68, 78a-b, and 102.

When flashing lights 68, controller 104 is configured in at least one aspect to only flash the icon light 68 that is positioned behind the icon corresponding to the condition that is alerting. Thus, when exit detection system 150 detects a patient exit and issues an alert, controller 104 is configured to flash only the light 68 positioned behind icon 70a (which corresponds to the exit detection system 150). The lights 68 positioned behind the other icons 70b-g may remain activated (or deactivated) in whatever manner in which they were previously activated (or deactivated) immediately prior to the exit detection alert. Thus, for example, if the icon light 68 positioned behind brake icon 70e was previously activated to display a steady green color prior to exit detection system 150 issuing an alert, controller 104 is configured in at least one aspect to continue to keep light 68 steadily activated with a green color while it flashes the light 68 (red) behind exit detection alert icon 70a during the exit detection alert.

User interface 62 communicates with controller 104 and allows the caregiver to control various aspects of exit detection system 150, such as, but not limited to, arming or disarming exit detection system 150, customizing a setting of exit detection system 150, such as customizing a sensitivity level of exit detection system 150 (FIG. 14, discussed in more detail below), and cancelling an alert issued by exit detection system 150. Other customizable settings for exit detection system 150 are possible.

Monitoring system 152 comprises a collection of sensors and a processing unit, such as controller 104, that processes the outputs from the collection of sensors to determine if any one or more of the components monitored by the sensors are in an undesired state. If any one or more are in an undesired state, and monitoring system 152 is armed, it issues an alert. In some aspects, monitoring system 152 includes side rail sensors 132, HOB angle sensors 134, height sensors 136, and brake sensors 138. Other types of sensors may additionally or alternatively be used for determining the state of one or more monitored conditions of the patient support apparatus 30. The particular structural details of monitoring system 152 can vary widely. An exemplary monitoring system is described in U.S. Pat. No. 8,844,076, filed on Jan. 27, 2014, entitled "Patient Handling Device Including Local Status Indication, One-Touch Fowler Angle Adjustment, and Power-On Alarm Configuration," the complete disclosure of which is hereby incorporated herein by reference. Other types of monitoring systems may be used.

Monitoring system 152 is configured to be armed and disarmed. When armed, bed monitoring system 152 issues an alert when at least one monitored condition of the patient support apparatus 30 is in an undesired state, which may include when one or more of the side rails are down, when the HOB angle is less than the preset angle, when the bed is not flat, or when the brake are not engaged. Controller 104 is configured, in at least one aspect, to synchronously flash lights 78a, 78b, and 102 in an amber color when bed monitoring system 152 issues an alert. Controller 104 may further be configured to synchronously flash the icon light 68 positioned behind bed monitor icon 70b in an amber color when bed monitoring system 152 issues an alert.

User interface 62 communicates with controller 104 and enables the caregiver to control one or more aspects of bed monitoring system 152. User interface 62 allows the caregiver to control various aspects of bed monitoring system 152, such as, but not limited to, navigating to a bed monitor control screen 350, arming or disarming bed monitoring system 152, and cancelling an alert issued by bed monitoring system 152. Display 64a displays information regarding bed monitoring system 152, such as, but not limited to, displaying a bed monitor control screen 350, and displaying an alert issued by bed monitoring system 152.

When the exit detection system 150 or bed monitoring system 152 issue an alert, the controller 104, in at least one aspect, triggers an auditory alarm. The auditory alarm may be stored in at least one audio playback circuit 146 connected to the controller 104 through SPI communication. Additionally, or alternatively, the audio playback circuit 146 is operated through a standalone switch. The audio playback circuit 146 stores one or more prerecorded audio files to be used as auditory alarms and plays them back. In one example, the audio playback circuit 146 stores one audio file corresponding to an alert issued by the exit detection system 150 and a second audio file corresponding to an alert issued by the bed monitoring system 152. The audio playback circuit 146 may be any suitable electronic chip that stores and plays back audio files, for example, the Digital Chip-Corder IC (ISD 2100) from Nuvoton. The signal from the positive and negative outputs of the audio playback circuit 146 is sent through a low pass filter to eliminate noise and inaudible frequencies.

The audio playback circuit 146 is connected to an audio amplifier 147, for example, the mono class-D TPA3112D1PWPR from Texas Instruments. The audio amplifier 147 increases the volume output by the audio playback circuit 146. The volume of the auditory alarm is controlled by the audio playback circuit 146. In one aspect, the volume of the audio playback circuit 146 is increased to meet International Electrotechnical Commission (IEC) standards for medical devices. The audio amplifier 147 has four gains set to the highest gain setting. The audio amplifier 147 outputs an amplified differential signal that is then passed through a filter. The audio amplifier 147 is connected to a speaker 148 which emits the amplified audio file. In one aspect, the audio amplifier 147 has four PWM differential speakers to drive the speaker 148. The speaker 148 may be a 4 ohm or 8 ohm speaker. As depicted in FIG. 4, the audio playback circuit 146, audio amplifier 147, and speaker 148 are external to the user interface 62. In an alternative aspect, the audio playback circuit 146, audio amplifier 147, and speaker 148 may be integrated into the user interface 62.

FIG. 2 illustrates one example of a motion control screen 154 that can be displayed on display 64a. Motion control screen 154 includes a plurality of controls, some or all of which can include touchscreen controls, non-touchscreen controls, or a combination thereof. The controls perform a variety of different functions, and the number, function, lay-out, size, and/or other characteristics of these controls may vary from what is shown in FIG. 2, and may also vary depending upon what screen is being displayed at a given time by display 64a. Motion control screen 154 may be displayed initially after the patient support apparatus 30 is powered on or switches to a wake mode, as explained in more detail below, or it may be displayed in response to a caregiver navigating to it from another screen.

Figures 14, 15, 16, 17:
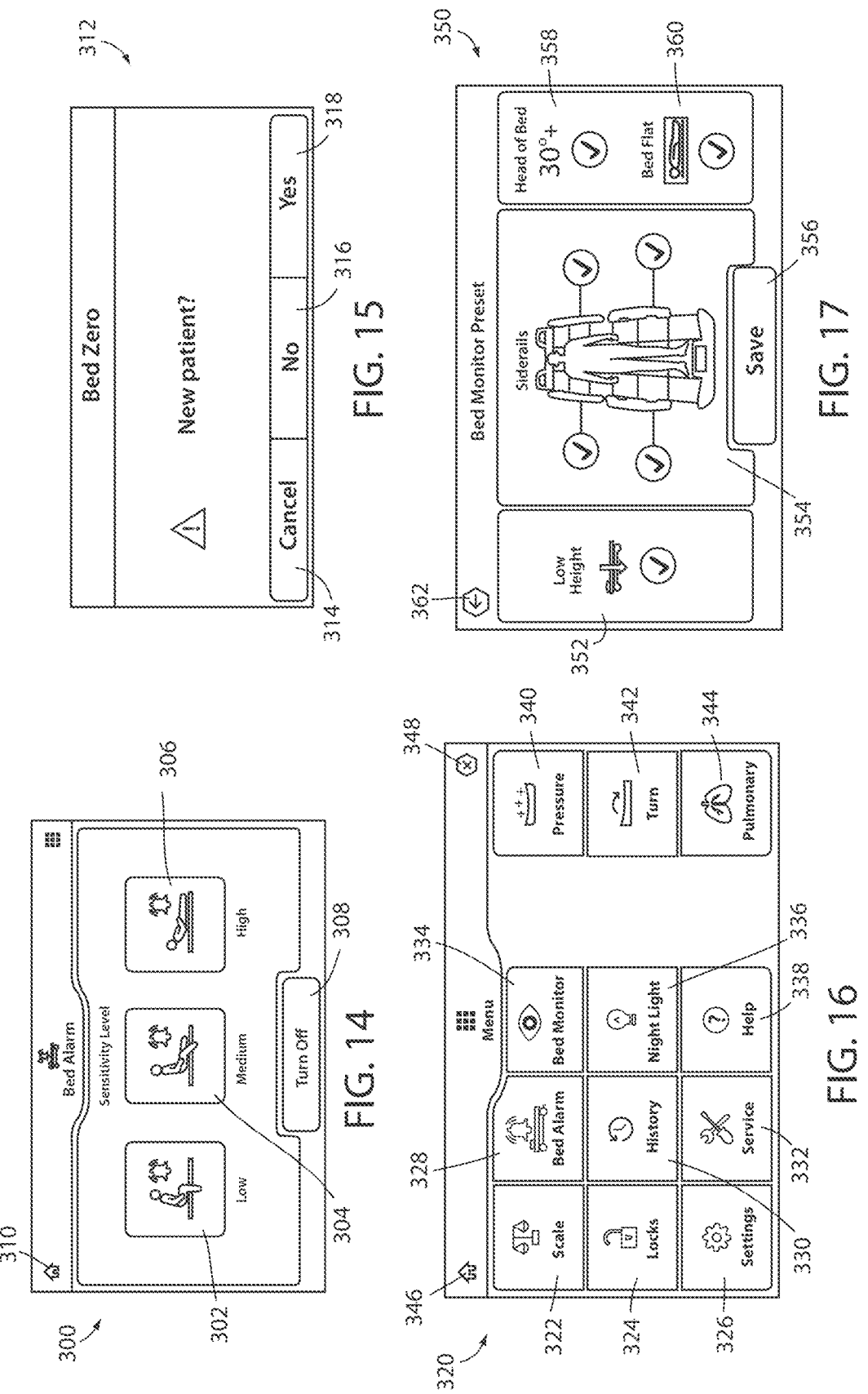
FIG. 14 is an illustrative bed alarm monitoring screen that may be displayed on the display of the first user interface.
FIG. 15 is an illustrative new patient screen that may be displayed on the display of the first user interface.
FIG. 16 is an illustrative menu screen that may be displayed on the display of the first user interface.
FIG. 17 is an illustrative monitoring system configuration screen that may be displayed on the display of the first user interface.

With reference to FIG. 14, in some aspects, controller 104 displays an exit detection control screen 300 on display 64a. The exit detection control screen 300 is used by a caregiver or other user to control aspects of exit detection system 150, and can include an arming control that enables the caregiver to arm and/disarm exit detection system 150. The arming control can set the sensitivity level of the exit detection system 150 to a low setting 302, a medium setting 304, or a high setting 306. The sensitivity level determines the displacement of a patient required for the controller 104 to issue an alert for the exit detection system 150. The exit detection system 150 can be disarmed by pressing the off control 308. The exit detection control screen 300 may have a home control 310 to dismiss the exit detection control screen 300 without any changes to the exit detection system 150 and return the user to a main menu (not shown).

With reference to FIG. 17, in some aspects, controller 104 displays a monitoring system control screen 350 on display 64*a*. The monitoring control screen 350 is used by a caregiver or other user to control aspects of monitoring system 152, and can include an arming control that enables the user to arm and/disarm monitoring system 152. The arming control can set a number of characteristics of the monitoring system 152 including the height 352 of patient support apparatus 30, the position of the side rails 354, the angle of the head of the bed 358, and the position of the bed 360 (i.e. bed flat). The caregiver may enable or disable the monitoring of each of the characteristics 352, 354, 358, and 360. Once the caregiver or other user has set the characteristics to their desired state, the user can use save control 356 to arm the system 152. The user can use exit control 362 to leave the monitoring control screen 350 and return to whichever screen was previously displayed on display 64*a*.

In FIG. 16, a menu screen 320 that may be displayed on display 64*a* is shown. The menu screen 320 can allow a caregiver or other user to navigate to various screens to show information about or to control patient support apparatus 30. The menu screen 320 includes a scale control 322; a lock control 324; a settings control 326; a bed alarm control 328; a history control 330; a service control 332; a monitoring system control 334; a night light control 336; a help control 338; a pressure control 340; a turn control 342; and a pulmonary control 344. Pressing the bed alarm control 328 causes the exit detection control screen 300 to appear on display 64*a*. Pressing the monitor system control 334 causes the monitoring system control screen 350 to appear on display 64*a*. Pressing the settings control 326 brings up another screen that allows the user to navigate to the global settings screen of FIG. 11. The menu screen 320 has a home control 346 to cause the home screen to appear on display 64*a*. The menu screen 320 has a cancel control 348 to dismiss the menu screen 320 and return to the previously displayed screen.

Returning to FIG. 2, for some aspects, controller 104 operates display 64*a* in multiple different modes, including a sleep mode and a wake mode. Controller 104 activates display 64*a* when the patient support apparatus 30 is in the wake mode and deactivates display 64*a* when the patient support apparatus 30 is in the sleep mode. Controller 104 switches from the wake mode to the sleep mode after a predetermined time period of inactivity at user interfaces 62, 80 has elapsed, i.e. after a timeout period. When in the sleep mode, controller 104 switches back to the wake mode and activates display 64*a* upon detecting that the user has touched display 64*a*, or another portion of any of user interfaces 62, 80.

During operation of patient support apparatus 30, controller 104 is configured to repetitively check to see whether each component in a set of components is in its desired state and, if any one or more of them are not, to issue a reminder to the caregiver to place the components in their desired state. In at least one aspect, the set of components and their desired states includes the following: exit detection system 150 (armed); monitoring system 152 (armed), brake 61 (activated), and power cord 112 (plugged into an electrical outlet). It will be understood that this set of components may be varied in different aspects and that, in some of those different aspects, the set of components that are repetitively monitored by controller 104 for reminder purposes may be customized by users of patient support apparatus 30. It will further be understood that the monitoring of the set of components for reminder purposes is carried out automatically and repetitively at all times that patient support apparatus 30 is powered on, and not just at times when display 64*a* is in the wake mode.

Still further, it will be understood that the repetitive monitoring of the set of components for reminder purposes is different from the monitoring that is carried out by monitoring system 152. The monitoring that is carried out by monitoring system 152 is only carried out when monitoring system 152 is armed. Additionally, the monitoring that is carried out by system 152 may be of a different set of components and/or conditions than the set of components that controller 104 monitors for reminder purposes. For example, in many aspects, monitoring system 152 monitors the position of one or more side rails 44, 46, 48, and/or 50, while controller 104 is not configured to monitor the side rails (in at least one aspect) for reminder purposes. Still further, the consequences of the monitoring carried out by controller 104 for purposes of reminders and for purposes of monitoring system 152 are different. If controller 104 detects a component that is in an undesired state for purposes of its reminder monitoring, it issues a reminder. In contrast, if controller 104 detects a component that is in an undesired state as defined by monitoring system 152, it issues an alert, rather than a reminder. As mentioned previously, controller 104 is configured, in at least some aspects, to flash lights 68, 78*a-b*, and/or 102 in response to an alert, and to pulse lights 68, 78*a-b*, and/or 102 in response to a reminder.

In addition to issuing a reminder via the pulsing of lights 68, 78*a-b*, and/or 102, controller 104 is configured to issue a reminder by displaying a reminder screen on display 64*a*. The particular reminder screen is, in at least one aspect, different for each of the different components that patient support apparatus 30 is configured to issue reminders for. Thus, for example, if brake 61 is deactivated, controller 104 displays a brake reminder screen, and if AC power cord 112 is not plugged in, controller 104 displays an AC power cord reminder screen that is different. Examples of the types of reminder screens that are displayable by controller 104 on display 64*a* are shown in FIGS. 5-10 and described in further detail below.

Before turning to the individual reminder screens shown in FIGS. 5-10, it should be noted that controller 104, in at least one aspect, is configured to display a corresponding reminder screen only once during a wake session of display 64*a*. That is, once display 64*a* is awake, controller 104 displays a reminder screen if any of the components for which reminders are set is in an undesired state. If the reminder screen is dismissed by the user (discussed more below), controller 104 does not display the reminder screen again unless display 64*a* first switches the sleep mode and then back to the wake mode. Upon re-entering the wake mode, controller 104 is configured to issue these reminder screens for any components that are not in their desired state when display 64*a* re-awakens. In this manner, a caregiver is typically only reminded once with a reminder screen for any given interaction with patient support apparatus 30, thereby allowing the caregiver to use display 64*a* for other functions while still reminding the caregiver of tasks that should be completed. In contrast, and as will be discussed more below, the pulsing of lights 68, 78*a-b*, and/or 102 continues at all times that patient support apparatus 30 is detected to not be in a proper configuration, regardless of whether a reminder screen is being displayed on display 64a and regardless of whether display 64a is in the wake mode or sleep mode.

Some non-limiting examples of reminder screens are provided in the FIGS. 5-10. It will be understood that the particular layouts of the reminder screens shown in FIGS. 5-10 are but one of a large variety of different ways in which controller 104 may present a reminder screen. It will also be understood that the display of any of the reminder screens of FIGS. 5-10 may occur shortly, or immediately, after display 64a switches from the sleep mode to the wake mode if the corresponding component was in the undesired state while display 64a was in the sleep mode. On the other hand, if the corresponding component is initially in its desired state when display 64a is woken from the sleep mode to the wake mode, the corresponding reminder screen will not be displayed until, and if, the user switches the state of the corresponding component to its undesired state. Still further, in some instances, the reminder screen may not be displayed at all if the only time the corresponding component is in its undesired state is when display 64a is in the sleep mode. In at least one alternative aspect, however, the reminder screens of FIGS. 5-10 are also displayed when display 64a is in the sleep mode and a change to the undesired state occurs. In this alternative aspect, the change to the corresponding undesired state acts as a trigger for waking display 64a, and controller 104 displays the corresponding reminder screen in response to this trigger.

Figures 5, 6, 7, 8:
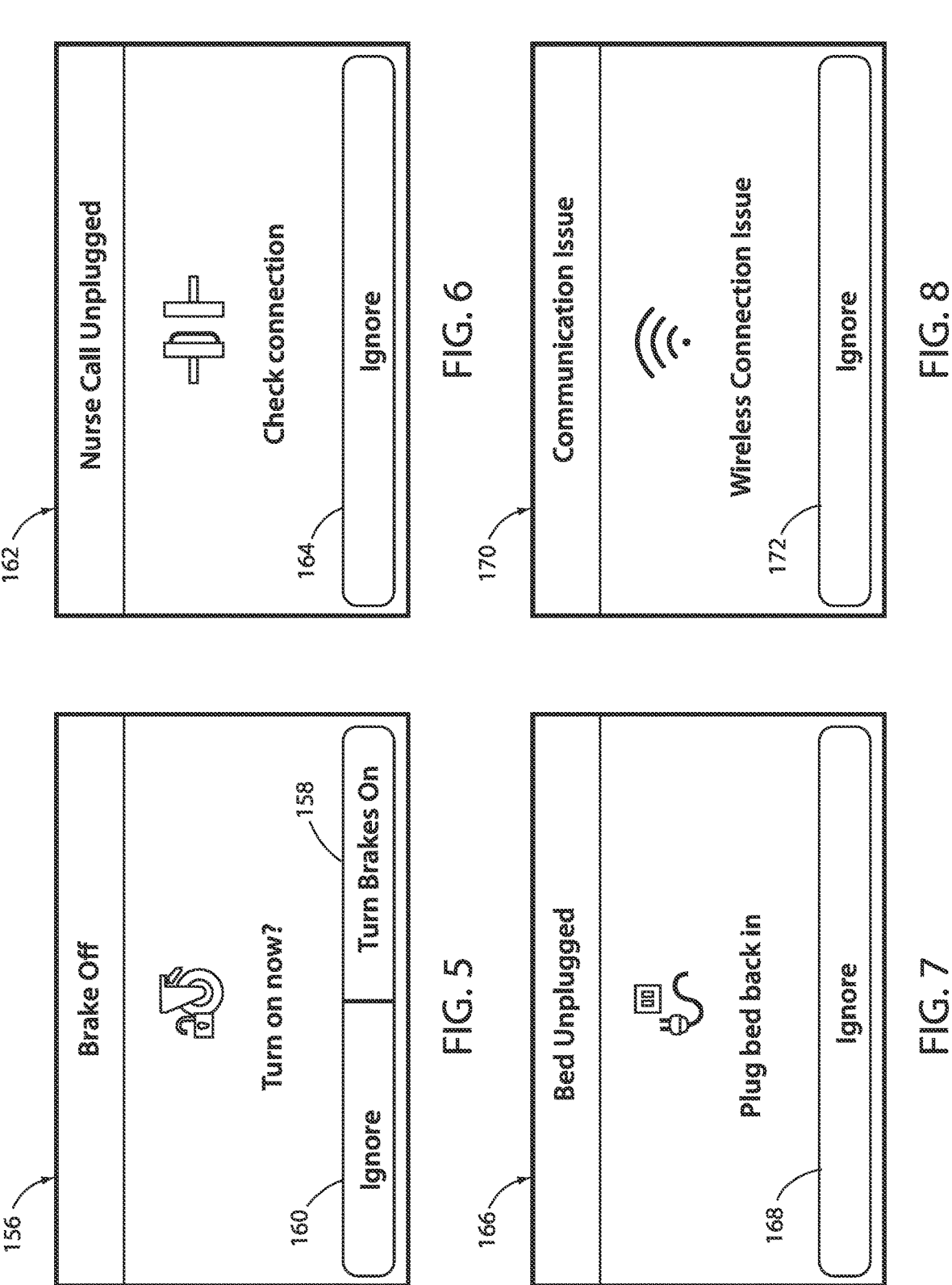
FIG. 5 is an illustrative brake reminder screen that may be displayed on a display of the first user interface.
FIG. 6 is an illustrative nurse call reminder screen that may be displayed on the display of the first user interface.
FIG. 7 is an illustrative power source reminder screen that may be displayed on the display of the first user interface.
FIG. 8 is an illustrative Wi-Fi reminder screen that may be displayed on the display of the first user interface.

FIG. 5 is an illustrative brake reminder screen 156 that is displayed on display 64a of user interface 62 of FIG. 2 when controller 104 detects that brake 61 is deactivated. Brake reminder screen 156 includes an activation control 158 and an ignore control 160. Upon user-activation of the activation control 158, controller 104 is operable to turn brake 61 on. The activation control 158 controls the state of brake 61, and automatically changes the state of the brake to the desired state, e.g. the engaged or on state. Upon user-activation of the ignore control 160, controller 104 is operable to clear the reminder screen 156 and does not turn brake 61 on. After clearing the reminder screen 156, controller 104 is operable to display the motion control screen 154 or another previously displayed screen on display 64a, or otherwise enable the caregiver to use user interface 62, and does not turn brake 61 on. The pulsing of lights 68, 78a-b, and/or 102 that is simultaneously triggered (with the display of brake reminder screen 156) by brake 61 being in the undesired state continues after reminder screen 156 is cleared, and continues until not only brake 61 is in its desired state, but all of the components for which reminders are issued are in their respective desired states.

FIG. 6 is an illustrative nurse call reminder screen 162 that may be displayed on display 64a of user interface 62 of FIG. 2 when nurse call cable 128 is not connected to a nurse call outlet 126, or wireless communication between patient support apparatus 30 and the nurse call outlet 126 is not functioning. Nurse call reminder screen 162 includes an ignore control 164. Upon user-activation of the ignore control 164, controller 104 is operable to clear the reminder screen 162. After clearing the reminder screen 162, controller 104 is operable to display the motion control screen 154 or another previously displayed screen on display 64a, or otherwise enable the caregiver to use user interface 62. Controller 104 is also operable to clear the reminder screen 162 if the caregiver couples nurse call interface 122 to the nurse call outlet 126 while the reminder screen 162 is being displayed.

In some aspects, controller 104 does not synchronously pulse lights 68, 78a-b, or 102 in response to nurse call interface 122 being disconnected from nurse call outlet 126. Instead, in such aspects, controller 104 activates the icon light 68 behind nurse call icon 70f and leaves it activated until the nurse call interface 122 is connected to the nurse call outlet 126, regardless of whether or not reminder screen 162 is cleared or not. The activation of the light 68 behind nurse call icon 70f may be carried out such that that light emits an amber color. Further, the activation of the amber color may be steady or pulsed.

FIG. 7 is an illustrative power source reminder screen 166 that may be displayed on display 64a of user interface 62 of FIG. 2. Controller 104 displays power source reminder screen 166 on display 64a when the power cord 112 is unplugged and the patient support apparatus 30 is not receiving external power from the external power source 108. Power source reminder screen 166 includes an ignore control 168. Upon user-activation of the ignore control 168, controller 104 is operable to clear the reminder screen 166. After clearing the reminder screen 166, controller 104 is operable to display the motion control screen 154 or another previously displayed screen on display 64a, or otherwise enable the caregiver to use user interface 62. Controller 104 is also operable to clear the reminder screen 166 if the caregiver plugs in the power cord 112 while the reminder screen 166 is being displayed. The pulsing of lights 68, 78a-b, and/or 102 that is simultaneously triggered (with the display of power source reminder screen 166) by power cord 112 being unplugged continues after reminder screen 166 is cleared, and continues until not only power cord 112 is plugged into an electrical outlet, but also until all of the components for which reminders are issued are in their respective desired states.

FIG. 8 is an illustrative Wi-Fi reminder screen 170 that may be displayed on display 64a of user interface 62 of FIG. 2. Controller 104 displays Wi-Fi reminder screen 170 on display 64a when the patient support apparatus 30 is not connected to Wi-Fi, e.g. if the Wi-Fi transceiver 116 is disconnected from a wireless access point 118 (or a server on network 120). Wi-Fi reminder screen 170 includes an ignore control 172. Upon user-activation of the ignore control 172, controller 104 is operable to clear the reminder screen 170. After clearing the reminder screen 170, controller 104 is operable to display the motion control screen 154 or another previously displayed screen on display 64a, or otherwise enable the caregiver to use user interface 62. Controller 104 is also operable to clear the reminder screen 170 if the caregiver connects the patient support apparatus 30 to Wi-Fi while the reminder screen 170 is being displayed.

In some aspects, controller 104 does not synchronously pulse lights 68, 78a-b, or 102 in response to wireless transceiver 116 being disconnected from local area network 120. Instead, in such aspects, controller 104 activates the icon light 68 behind wireless communication icon 70g and leaves it activated until the network transceiver 116 is able to communicate with local area network 120, regardless of whether or not reminder screen 170 is cleared or not. The activation of the light 68 behind wireless communication icon 70g may be carried out such that that light emits an amber color. Further, the activation of the amber color may be steady or pulsed.

FIG. 9 is an illustrative bed exit reminder screen 174 that may be displayed on display 64a of user interface 62 of FIG. 2. Controller 104 displays bed exit reminder screen 174 on display 64a when all three of the following conditions occur: exit detection system 150 is disarmed, a patient is present on patient support apparatus 30, and memory 106 includes a desired arming state for exit detection system 150. The desired arming state may refer to a global setting indicating that exit detection system 150 should be turned on/off for all patients, or it may refer to a patient-specific setting indicating that exit detection system 150 should be turned on/off only for the specific patient currently assigned to patient support apparatus 20. The patient-specific setting is re-set to the same value as the global setting whenever a new patient is assigned to patient support apparatus 20.

Thus, for example, if a first patient has the patient-specific reminder setting turned off for exit detection system 150 while the global reminder setting for exit detection system 150 is turned on, controller 104 will not issue any reminders to turn on exit detection system 150 while that patient is assigned to the patient support apparatus (unless the patient-specific reminder is changed to the on state while the patient is assigned to the patient support apparatus). However, when a new patient is assigned to the patient support apparatus, controller 104 will automatically change the patient-specific reminder setting to on (in order to match the global reminder setting that is on). Reminders will therefore be issued to turn on exit detection system 150 for as long as the new patient is assigned to the patient support apparatus (or until the caregiver turns off the patient specific reminder for the exit detection system 150).

If the user desires exit detection system 150 to always be armed for all patients, the user is able to set this desired global state in memory 106 by, for example, accessing the screen shown in FIG. 11 and selecting the global reminder setting for the exit detection system 150, as discussed more below with respect to FIG. 11. If the user does not want a reminder issued for all patients to arm exit detection system 150, he or she can un-select the global reminder setting in FIG. 11. The control of patient-specific settings for exit detection system 150 is carried out through screens 174 (FIG. 9) and screen 310 (FIG. 14). When a caregiver activates the "turn off" option of screen 174, controller 104 automatically sets the patient specific reminder setting for the exit detection system 150 to the off state (and does not change the global setting). When a caregiver arms the exit detection system 150, such as by selecting the exit detection control icon 308 (which toggles between the messages "turn off" and "turn on"), controller 104 automatically sets the patient specific reminder setting for the exit detection system 150 to the on state (and does not change the global setting).

Bed exit reminder screen 174 includes an off control 178 and a dismiss control 180. Upon user-activation of the off control 178, controller 104 is operable to change the patient-specific setting for exit detection system 150 from on to off. This patient-specific setting is stored in memory 106. The activation of the off control 178 does not change the global setting that is stored in memory for exit detection system 150 that applies to all patients (except this setting is overridden by a contrary setting for the specific patient currently assigned to patient support apparatus 20).

If the caregiver desires to turn the reminder for the exit detection system 150 back on for the specific patient assigned to patient support apparatus 20, the caregiver can do so by using the exit detection control screen 300 (FIG. 14). That is, controller 104 is configured to automatically switch the exit detection reminder setting back to the on state for a specific patient whenever the exit detection system 150 is armed, or re-armed. Controller 104 does not, however, change the state of the global exit detection reminder setting in response to the arming or disarming of exit detection system 150. Instead, changes to the global settings for exit detection system 150 can only be made via global setting screen 190 (FIG. 11).

Upon user-activation of the dismiss control 180, controller 104 is operable to clear the reminder screen 174 and does not arm exit detection system 150. After clearing the reminder screen 174, controller 104 is operable to display the motion control screen 154 or another previously displayed screen on display 64a, or otherwise enable the caregiver to use user interface 62. The pulsing of lights 68, 78a-b, and/or 102 that is simultaneously triggered (with the display of bed exit reminder screen 174) by exit detection system 150 being disarmed continues after reminder screen 174 is cleared, and continues until not only exit detection system 150 is armed, but all of the components for which reminders are issued are in their respective desired states. In an alternative aspect, the pulsing of lights 68, 78a-b, and/or 102 is not simultaneously triggered by the exit detection system 150 being disarmed. In yet another aspect, the exit detection system 150 is not tied to the lights at all.

FIG. 10 is an illustrative monitoring system reminder screen 182 that may be displayed on display 64a of user interface 62 of FIG. 2. Controller 104 displays monitoring system reminder screen 182 on display 64a when all three of the following conditions occur: monitoring system 152 is disarmed, a patient is present on patient support apparatus 30, and memory 106 includes a desired arming state for monitoring system 152. The desired arming state may refer to a global setting indicating that monitoring system 152 should be turned on/off for all patients, or it may refer to a patient-specific setting indicating that monitoring system 152 should be turned on/off only for the specific patient currently assigned to patient support apparatus 20. The patient-specific setting is re-set to the same value as the global setting whenever a new patient is assigned to patient support apparatus 20.

Thus, for example, if a first patient has the patient-specific reminder setting turned off for monitoring system 152 while the global reminder setting for monitoring system 152 is turned on, controller 104 will not issue any reminders to turn on monitoring system 152 while that patient is assigned to the patient support apparatus (unless the patient-specific reminder is changed to the on state while the patient is assigned to the patient support apparatus). However, when a new patient is assigned to the patient support apparatus, controller 104 will automatically change the patient-specific reminder setting to on (in order to match the global reminder setting that is on). Reminders will therefore be issued to turn on monitoring system 152 for as long as the new patient is assigned to the patient support apparatus (or until the caregiver turns off the patient specific reminder for the monitoring system 152).

If the user desires monitoring system 152 to always be armed for all patients, the user is able to set this desired global state in memory 106 by, for example, accessing the screen shown in FIG. 11 and selecting the global reminder setting for the monitoring system 152, as discussed more below with respect to FIG. 11. If the user does not want a reminder issued for all patients to arm monitoring system 152, he or she can un-select the global reminder setting in FIG. 11. The control of patient-specific settings for monitoring system 152 is carried out through screens 182 (FIG. 10) and screen 362 (FIG. 17). When a caregiver activates the "turn off" option of screen 182, controller 104 automatically sets the patient specific reminder setting for the monitoring system 152 to the off state (and does not change the global setting). When a caregiver arms the monitoring system 152, such as by selecting various features to be armed on screen 362 and pressing "save," controller 104 automatically sets the patient-specific reminder setting for the monitoring system 152 to the on state (and does not change the global setting).

Monitoring system reminder screen 182 (FIG. 10) includes an off control 186 and a dismiss control 188. Upon user-activation of the off control 186, controller 104 is operable to turn off the monitoring system 152 for the current patient and clear the reminder screen 182. This patient-specific setting is stored in memory 106. The activation of the off control 186 does not change the global setting that is stored in memory for monitoring system 152 that applies to all patients (except this setting is overridden by a contrary setting for the specific patient currently assigned to patient support apparatus 20).

If the caregiver desires to turn the reminder for the monitoring system 152 back on for the specific patient assigned to patient support apparatus 20, the caregiver can do so by using the monitoring system control screen 320 (FIG. 16) to arm the monitoring system 152 That is, controller 104 is configured to automatically switch the monitoring system reminder setting back to the on state for a specific patient whenever the monitoring system 152 is armed, or re-armed. Controller 104 does not, however, change the state of the global monitoring system reminder setting in response to the arming or disarming of monitoring system 152. Instead, changes to the global settings for monitoring system 152 can only be made via global setting screen 190 (FIG. 11).

Upon user-activation of the dismiss control 188, controller 104 is operable to clear the reminder screen 182 and does not arm monitoring system 152. After clearing the reminder screen 182, controller 104 is operable to display the motion control screen 154 or another previously displayed screen on display 64a, or otherwise enable the caregiver to use user interface 62. The pulsing of lights 68, 78a-b, and/or 102 that is simultaneously triggered (with the display of monitoring reminder screen 182) by monitoring system 152 being disarmed continues after reminder screen 182 is cleared, and continues until not only monitoring system 152 is armed, but all of the components for which reminders are issued are in their respective desired states. In an alternative aspect, the pulsing of lights 68, 78a-b, and/or 102 is not simultaneously triggered by the monitoring system 152 being disarmed.

From the foregoing description, it can be seen that controller 104 is configured to issue a plurality of different reminder screens when various components of patient support apparatus 30 are in undesired states. For many of these components, patient support apparatus 30 is configured to also pulse lights 68, 78a-b, and 102 to serve as a visual reminder to the caregiver, and to continue to pulse these lights until all of the components of the patient support apparatus 30 are in their desired state. In this manner, lights 68, 78a-b, and 102 continue to be pulsed while the caregiver may be busy performing other duties, and this continued pulsing serves as a gentle, yet persistent, reminder that he or she needs to change at least one more condition of patient support apparatus 30 before it will be in its desired state. To see which specific condition(s) need to be changed, he or she can consult dashboard 64b and see which of icons 70a-g are being illuminated in an amber color. Those icons 70a-g that correspond to components that are in their desired states are illuminated with a green color. Dashboard 64b therefore provides an easy to read visual indicator of what, if any, components are not currently in their desired states.

As mentioned previously, patient support apparatus 30 is configurable by caregivers to always issue reminders to arm exit detection system 150 and/or monitoring system 152 when controller 104 detects that either or both of these systems are disarmed. This is accomplished by accessing a global setting screen 190, such as shown in FIG. 11.

FIG. 11 is an illustrative global settings screen 190 that is displayable on display 64a of user interface 62 of FIG. 2. Access to screen 190 may be accomplished by selecting a settings control (not shown) provided on the motion control screen 154 or on another screen shown on display 64a, or elsewhere on user interface 62. Global settings screen 190 includes multiple controls for selecting whether arming of exit detection system 150 is required or is not required for new patients, whether arming of monitoring system 152 is required or is not required for new patients, and the preset angle for the head-of-bed (HOB) angle for new patients. The settings for the new patient protocol are stored in memory 106.

The global settings screen 190 includes setting controls 192a, 192b and associated indicators 194a, 194b for each of the settings that can be selected. The setting controls 192a, 192b may alternatively be referred to as global controls. In the illustrated example, a first setting control 192a is associated with exit detection system 150 and a second setting control 192b is associated with monitoring system 152. Text and/or graphics, or other forms of visual content, are associated with the setting controls 192a, 192b, to indicate which of the settings correspond to which control.

The setting indicators 194a, 194b show whether the associated setting is currently being applied or not. The setting indicators 194a, 194b are generated on the screen 190 in a first color or with a first graphic when the associated setting is currently being applied and in a second color or with second graphic when the associated setting is not currently being applied. In the illustrated example of screen 190, the exit detection system setting control 192a and the monitoring system setting control 192b are both currently being applied, and their associated indicators 194a, 194b are generated on the screen 190 in green with a check mark. When a setting is not selected, the associated indicator is generated on the screen 190 in gray without a check mark. The setting indicators 194a, 194b may alternatively employ text or graphics, or other forms of visual content, to indicate the currently applied settings.

With the setting controls 192a, 192b selected as shown in FIG. 11, the globally desired state of both exit detection system 150 and monitoring system 152 is the armed state, and controller 104 will issue a reminder to remind the caregiver to arm these systems 150, 152 if the patient is present on the patient support apparatus 30 and either system 150, 152 is disarmed.

Global settings screen 190 also includes a HOB angle state control 196. Pressing the state control 196 switches the preset HOB angle between 30 degrees and 45 degrees. In FIG. 11, the preset HOB angle is shown as being 30 degrees. Upon user-activation of the HOB angle state control 196, controller 104 is operable to change the default preset HOB angle to 45 degrees. Subsequent selection of the HOB angle preset state control 196 changes the default preset HOB angle back to 30 degrees. In some aspects, monitoring system 152 monitors the HOB angle and, when armed, issues an alert if the HOB angle dips below the threshold chosen on global settings screen 190.

The global settings screen 190 also includes a return control 198 for returning to the motion control screen 154

(FIG. 2). Upon user-activation of the return control 198, controller 104 is operable to display the motion control screen 154 on display 64a.

Figure 12A:
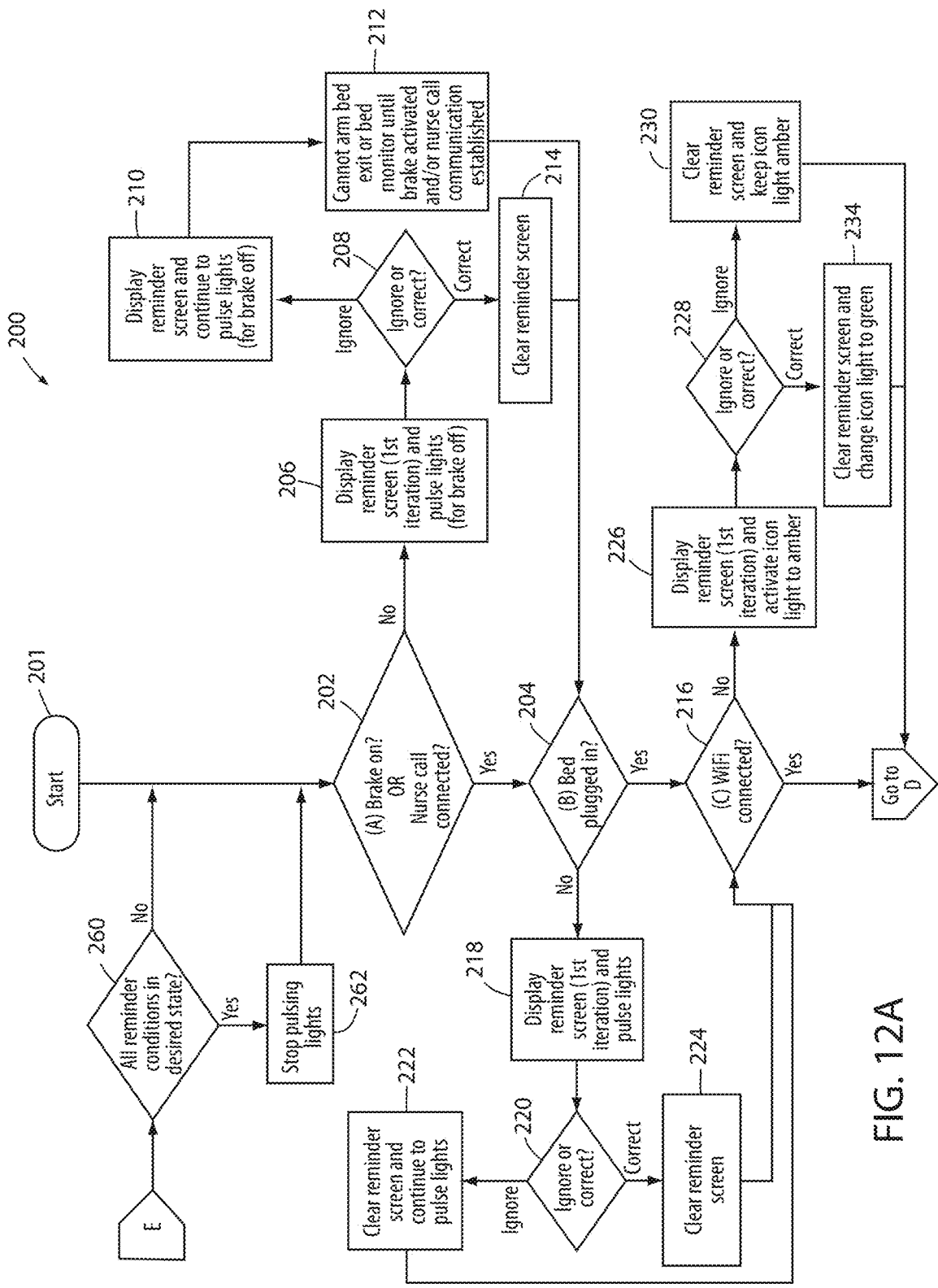
FIGS. 12A-12C are flow diagrams of a reminder management algorithm executed by a controller associated with the first and/or second user interfaces.
Figure 12B:
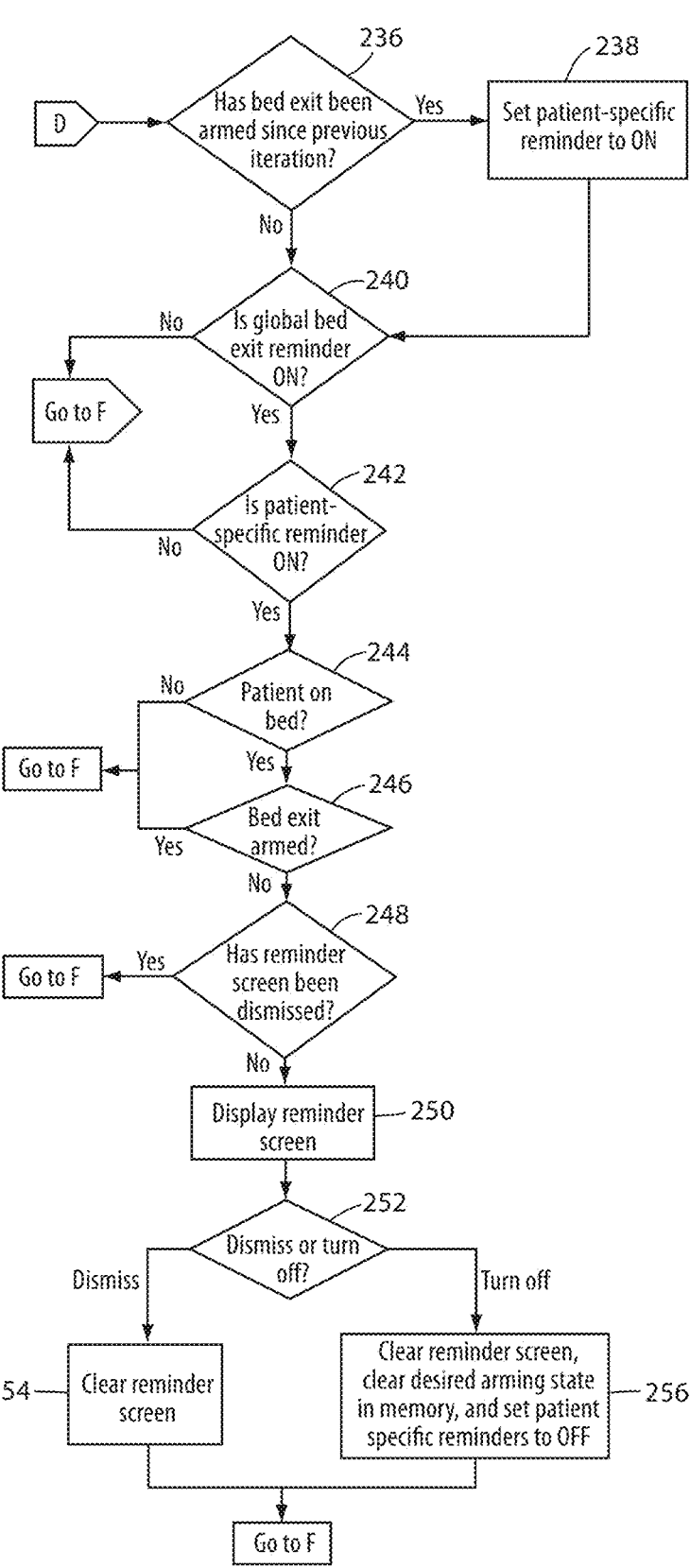
Figure 12C:
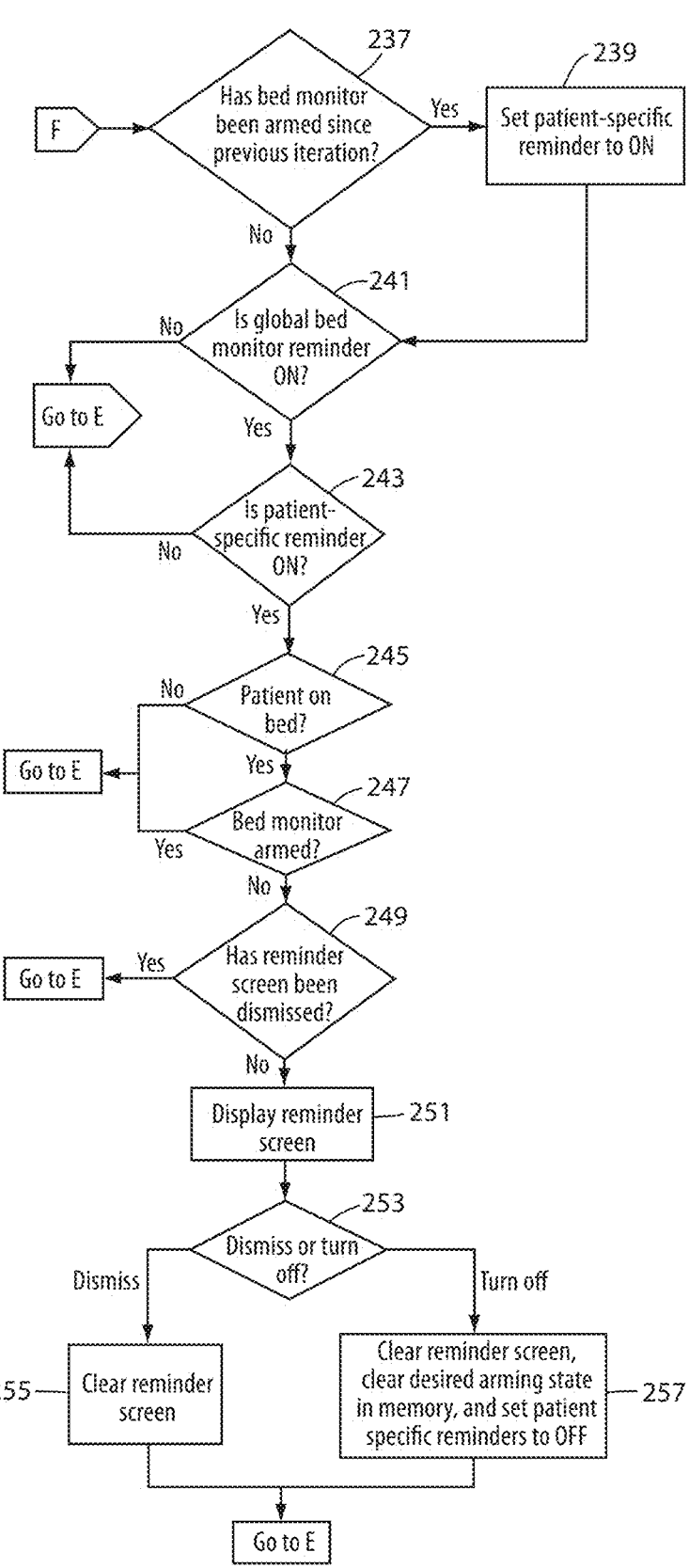

FIGS. 12A-12C depict a flow diagram of a reminder management algorithm 200 executed by controller 104. Reminder management algorithm 200 controls what form the various reminders take, when they are issued, and what effect, if any, they may have on other functionality of patient support apparatus 30. In some aspects, only a single reminder screen is displayed at a given time. In such situations, if multiple components are in their undesired states simultaneously, controller 104 displays the reminder screens serially. The particular order in which the reminder screens are displayed may be configurable by the user and/or changed in different aspects.

Algorithm 200 starts at a start step 201 (FIG. 12A). As noted previously, algorithm 200 is configured in at least one aspect to be substantially continuously executed upon power up of patient support apparatus 30. Accordingly, start step 201 commences, in at least some aspects, at the time, or shortly after the time, patient support apparatus 30 is powered on.

From step 201, controller 104 proceeds to step 202 where it determines if brake 61 (FIG. 1) is on and if nurse call interface 122 (FIG. 4) is communicatively coupled to a nurse call outlet 126. This determination is made based on input from the brake sensors 138 and the nurse call sensors 144. If it is determined that brake 61 is on and the nurse call interface 122 is connected, controller 104 proceeds to step 204. If brake 61 is off and/or nurse call interface 122 is not communicatively coupled to nurse call outlet 126, controller proceeds to step 206.

At step 206, controller 104 displays the corresponding reminder screen (e.g. reminder screen 156 of FIG. 5 or reminder screen 162 of FIG. 6) and begins pulsing lights 68, 78a, 78b, and 102 if brake 61 is off (and if these lights were not previously pulsing). If these lights were previously pulsing, controller 104 continues to pulse them. If brake 61 is on but nurse call interface 122 is not communicatively coupled to a nurse call outlet 126, controller 104, in at least one aspect, is configured to not pulse lights 68, 78a, 78b and 102, but instead activates the light 68 behind nurse call icon 70f in a steady amber color.

It will be understood that, for all of the steps of algorithm 200 that refer to the pulsing of lights (including, but not limited to, step 206), such pulsing refers to the synchronous pulsing of lights 68, 78a, 78b, and 102 that creates the breathing or glowing effect previously described. Further, it will be understood that all references to the pulsing of lights 68 refer to, in at least some aspects, the pulsing of the specific icon light 68 that corresponds to the component that is not in its desired state. Thus, if brake 61 is off, controller 105 pulses the icon light 68 at step 206 that is positioned behind icon 70e. If the other components corresponding to the other icons 70a-d and 70f-g are all in their desired state, controller 104 illuminates the lights 68 behind these icons in a steady green color. Thus, only the icons 70a-g that correspond to components not in their desired state are pulsed, in at least some aspects. In other aspects, the icons 70a-g that correspond to components not in their desired state are steadily illuminated in an amber color. In still other aspects, some icons 70a-g that correspond to components not in their desired state are pulsed while others of those icons 70a-g that correspond to components not in their desired state are illuminated with a steady color, such as amber. Still other variations are possible.

After step 206 (FIG. 12A), controller 104 proceeds to step 208 wherein it determines if the caregiver has ignored the reminder or corrected the state of brake 61 and/or nurse call interface 122. For example, if controller 104 determines that the ignore control 160 on the brake reminder screen 156 has been selected or that the ignore control 164 on the nurse call reminder screen 162 has been selected, then controller 104 proceeds to step 210. At step 210, controller 104 clears the reminder screen 156 and/or 162 from display 64a, but continues to pulse the lights (if they were pulsed at step 206). Clearing reminder screen 156 and/or 162 allows the caregiver to utilize display 56a for performing other tasks, including taking corrective action with respect to brake 61.

After step 210, controller 104 proceeds to step 212 and prevents the arming of exit detection system 150 and/or monitoring system 152. When brake 61 is not engaged or the nurse call interface 122 is disconnected, patient support apparatus 30 is configured to prevent exit detection system 150 and/or monitoring system 152 from being armed. If the state of brake 61 and/or nurse call interface 122 are later corrected, controller 104 re-enables arming of exit detection system 150 and/or monitoring system 152. This feature encourages the caregivers to remember to arm brake 61.

If, at step 208, controller 104 determines that the brake activation control 158 on the brake reminder screen 156 has been selected and/or that the nurse call interface 122 has been connected to a nurse call outlet 126, then controller 104 proceeds to step 214 in which the reminder is cancelled. Cancelling the reminder at step 214 includes clearing the reminder screen. It may also include ceasing the pulsing of the lights 68, 78a,b, and 102, depending upon the conditions of the other components that are monitored for reminders by controller 104, as will be discussed further below in more detail with respect to step 260. From step 214, controller 104 proceeds to step 204.

It is noted that while FIG. 12A shows the state of brake 61 and the nurse call interface 122 being checked simultaneously at step 202, this is merely done for purposes of visual brevity, and that controller 104 actually checks these states serially, and that it may do so in any order. Additionally, algorithm 200 may be modified to only check the state of brake 61 or only check the state of the nurse call interface 122, or in some aspects, to skip step 202 altogether.

At step 204 (FIG. 12A), controller 104 determines if the patient support apparatus 30 is plugged in, e.g. if the power cord 112 is plugged into the wall outlet 114 (FIG. 1) and is receiving external power from the external power source 108, based on signals from the power source sensors 140. If it is determined that the patient support apparatus 30 is plugged in to the external power source 108, controller 104 proceeds to step 216 and determines if the patient support apparatus 30 is connected to Wi-Fi.

If, at step 204, controller 104 determines that patient support apparatus 30 is unplugged, controller 104 proceeds to step 218 and issues a reminder to plug in the power cord 112. In one example, the power cord reminder comprises displaying the power cord reminder screen 166 (FIG. 7) on display 64a and pulsing lights 68, 78a, 78b, and 102.

After step 218, controller 104 proceeds to step 220 and determines if the caregiver has ignored the reminder or corrected the state of the power cord 112. For example, if controller 104 determines that the ignore control 168 on the power reminder screen 166 has been selected, then controller 104 proceeds to step 222 and clears the reminder screen 166. Controller 104, however, continues to pulse the lights 68, 78a, 78b, and 102 at step 222. The clearance of the reminder screen and continued pulsing of the lights allows the caregiver to operate user interface 62, including display 64a, while still reminding the caregiver that corrective action should be taken.

If, at step 220 (FIG. 12A), controller 104 determines that the power cord 112 has been plugged in, then controller 104 proceeds to step 224 in which the reminder is cancelled. Cancelling the reminder at step 224 includes clearing the power reminder screen 166 from display 64a. Cancelling the reminder at step 224 may also include ceasing the pulsing of the lights 68, 78a, 78b, and 102, depending upon the conditions of the other components that are monitored for reminders by controller 104, as will be discussed further below in more detail with respect to step 260. From step 224, controller 104 proceeds to step 216.

At step 216, controller 104 determines if the patient support apparatus 30 is connected to Wi-Fi, e.g. if the Wi-Fi transceiver 116 is connected to the wireless access point 118 (FIG. 3), based on input from the Wi-Fi connection sensor 142. If it is determined that the patient support apparatus 30 is connected to Wi-Fi, then controller 104 proceeds to step 236 (FIG. 12B).

If, at step 216 (FIG. 12A), controller 104 determines that patient support apparatus 30 is not connected to Wi-Fi, controller 104 proceeds to step 226 and issues a reminder. In one example, the Wi-Fi reminder comprises displaying the Wi-Fi reminder screen 170 (FIG. 8) on display 64a and pulsing lights 68, 78a, 78b, and 102. In another aspect, the reminder issued at step 226 omits pulsing of the lights 68, 78a, 78b, and 102, and instead only illuminates the specific icon light 68 positioned behind icon 70g in an amber color. Other variations may, of course, be implemented.

After issuing the reminder at step 226, controller 104 proceeds to step 228 where it determines if the caregiver has ignored the reminder or corrected the state of the Wi-Fi connection. For example, if controller 104 determines that the ignore control 172 on the Wi-Fi reminder screen 170 has been selected, then controller 104 proceeds to step 230 and clears the Wi-Fi reminder screen 170 from display 64a so that the caregiver can use user interface 62. In some aspects, controller 104 continues to pulse lights 68, 78a, 78b, and 102. In other aspects, controller 104 merely keeps icon 70g illuminated in a steady amber color at step 230. In either aspect, the clearance of the reminder screen and the continued activation of one or more lights allows the caregiver to operate user interface 62, including display 64a, while still reminding the caregiver that corrective action should be taken.

If, at step 2228, controller 104 determines that the Wi-Fi transceiver 116 has successfully established communication with the wireless access point 118 (and/or a specific server on network 120), then controller 104 proceeds to step 234 in which the reminder is cancelled. Cancelling the issued reminder at step 234 includes clearing the Wi-Fi reminder screen 170 from display 64a. Cancelling the reminder at step 234 may also include ceasing the pulsing of the lights 68, 78a, 78b, and 102, depending upon the conditions of the other components that are monitored for reminders by controller 104, as will be discussed further below in more detail with respect to step 260. Cancelling the issued reminder at step 234 may also, or alternatively, include changing the activation of the icon light 68 positioned behind icon 70g to a steady green color.

From step 216, controller 104 proceeds to step 236, which is illustrated in FIG. 12B. At step 236, controller 104 determines if personnel at the healthcare facility (e.g. caregivers) have armed the exit detection system 150 of the patient support apparatus 30 since the previous iteration of algorithm 200. This is determined by consulting memory 106, which stores the settings selected by the caregiver, or other authorized personnel, using global setting screen 190 (FIG. 11) and the exit detection control screen 300 (FIG. 14). If controller 104 determines at step 236 that the exit detection system 150 has not been armed since the previous iteration, it proceeds to step 240. If controller 104 determines at step 236 that the exit detection system 150 has been armed since the previous iteration, it proceeds to step 238. At step 238, the controller 104 sets the bed exit patient-specific reminder to the on state and proceeds to step 240.

At step 240 (FIG. 12B), the controller 104 determines whether the global bed exit reminder is on. This is determined by consulting memory 106, which stores the settings selected by the caregiver, or other authorized personnel, using global setting screen 190 (FIG. 11). If the controller 104 determines at step 240 the global bed exit reminder is in the off state, the controller 104 proceeds to step 237 (FIG. 12C). If the controller 104 determines at step 240 the global bed exit reminder is in the on state, the controller 104 proceeds to step 242. In another aspect, the controller 104 may skip step 240 and go straight to step 242.

At step 242 (FIG. 12B), the controller 104 determines whether the patient-specific bed exit reminder is on. This is determined by consulting memory 106, which stores the settings selected by the caregiver, or other authorized personnel, using exit detection control screen 300 (FIG. 14). If the patient-specific bed exit reminder is off, the controller 104 proceeds to step 237 (FIG. 12C). If the patient-specific bed exit reminder is on, the controller 104 proceeds to step 244.

At step 244 (FIG. 12B), controller 104 determines if there is a patient on the patient support apparatus 30, based at least in part on input from the force sensors 130 (FIG. 4). If it is determined that there is no patient on patient support apparatus 30, controller 104 proceeds to step 237 (FIG. 12C). If it is determined at step 244 that a patient is present on patient support apparatus 30, controller 104 proceeds to step 246 and determines if exit detection system 150 is armed. In some aspects, a delay may be followed by controller 104 before proceeding from step 244 to step 246 in order to give the caregiver some time between the patient entering patient support apparatus 30 and the issuance of a reminder to arm exit detection system 150.

If, at step 246 (FIG. 12B), it is determined that exit detection system 150 is armed, the controller proceeds to step 237 (FIG. 12C). If, at step 246, it is determined that exit detection system 150 is disarmed, then controller 104 proceeds to step 248 and determines whether the bed exit reminder screen 174 (FIG. 9) has been dismissed. If, at step 248, it is determined that the bed exit reminder screen 174 (FIG. 9) has not been dismissed, the controller 104 proceeds to step 251 and issues a reminder to the caregiver to arm exit detection system 150. The reminder comprises displaying the corresponding reminder screen on display 64a (e.g. bed exit reminder screen 174 (FIG. 9)). If, at step 248, it is determined that the bed exit reminder screen 174 (FIG. 9) has been dismissed, the controller 104 proceeds to step 237 (FIG. 12C).

From step 250, controller 104 proceeds to step 252 and determines if the caregiver has dismissed the reminder or turned off the desired arming state for system 150. For example, if controller 104 determines that the dismiss control 180 on the bed exit reminder screen 174 has been selected, then controller 104 proceeds to step 254. At step 254, controller 104 clears the reminder screen 174. The clearance of the reminder screen allows the caregiver to operate user interface 62, including display 64*a*. From step 254, the controller 104 proceeds to step 237 (FIG. 12C)

If, at step 252 (FIG. 12B), controller 104 determines that the off control 178 on the bed exit reminder screen 174 has been selected, then controller 104 proceeds to step 256. At step 256, controller 104 clears the reminder screen from display 64*a* and clears the desired arming state for exit detection system 150 in memory 106. Thus, off control 178 provides a supplemental manner for a caregiver to change the desired arming state of system 150 (in addition to global setting control screen 190 (FIG. 11)). The desired arming state of system 150 can also be changed using exit detection control screen 300 (FIG. 14, described in more detail below). In some aspects, the change to the desired arming states made at step 256 carries over to all future iterations of algorithm 200 until a new patient is assigned to patient support apparatus 30. In other aspects, the change to the desired arming states made at step 256 carries over to all future iterations of algorithm 200, including new patients that are assigned to patient support apparatus 30. From step 256, controller 104 proceeds to step 237 (FIG. 12C).

At step 237 (FIG. 12C), controller 104 determines if personnel at the healthcare facility (e.g. caregivers) have armed the monitoring system 152 of the patient support apparatus 30 since the previous iteration of algorithm 200. This is determined by consulting memory 106, which stores the settings selected by the caregiver, or other authorized personnel, using global setting screen 190 (FIG. 11) and the monitoring system control screen 350 (FIG. 17). If controller 104 determines at step 237 that the monitoring system 152 has not been armed since the previous iteration, it proceeds to step 241. If controller 104 determines at step 237 that the monitoring system 152 has been armed since the previous iteration, it proceeds to step 239. At step 239, the controller 104 sets the patient-specific monitoring reminder to the on state and proceeds to step 241.

At step 241 (FIG. 12C), the controller 104 determines whether the global monitoring reminder is on. This is determined by consulting memory 106, which stores the settings selected by the caregiver, or other authorized personnel, using global setting screen 190 (FIG. 11). If the controller 104 determines at step 241 the global monitoring reminder is in the off state, the controller 104 proceeds to step 260 (FIG. 12A). If the controller 104 determines at step 241 the global monitoring reminder is in the on state, the controller 104 proceeds to step 243. In another aspect, the controller 104 may skip step 241 and go straight to step 243.

At step 243 (FIG. 12C), the controller 104 determines whether the patient-specific monitoring reminder is on. This is determined by consulting memory 106, which stores the settings selected by the caregiver, or other authorized personnel, using monitoring control screen 350 (FIG. 17). If the patient-specific bed exit reminder is off, the controller 104 proceeds to step 260 (FIG. 12A). If the patient-specific bed exit reminder is on, the controller 104 proceeds to step 245.

At step 245 (FIG. 12C), controller 104 determines if there is a patient on the patient support apparatus 30, based at least in part on input from the force sensors 130 (FIG. 4). If it is determined that there is no patient on patient support apparatus 30, controller 104 proceeds to step 260 (FIG. 12A). If it is determined at step 245 that a patient is present on patient support apparatus 30, controller 104 proceeds to step 247 and determines if monitoring system 152 is armed. In some aspects, a delay may be followed by controller 104 before proceeding from step 245 to step 247 in order to give the caregiver some time between the patient entering patient support apparatus 30 and the issuance of a reminder to arm monitoring system 152.

If, at step 247 (FIG. 12C), it is determined that monitoring system 152 is armed, the controller 104 proceeds to step 260 (FIG. 12A). If, at step 247, it is determined that monitoring system 152 is disarmed, then controller 104 proceeds to step 249 and determines whether the monitoring system reminder screen 182 (FIG. 10) has been dismissed. If, at step 249, it is determined that the monitoring system reminder screen 182 (FIG. 10) has not been dismissed, the controller 104 proceeds to step 251 and issues a reminder to the caregiver to arm monitoring system 152. The reminder comprises displaying the corresponding reminder screen on display 64*a* (e.g. monitoring system reminder screen 182 (FIG. 10)). If, at step 249, it is determined that the monitoring system reminder screen 182 (FIG. 10) has been dismissed, the controller 104 proceeds to step 260 (FIG. 12A).

From step 251, controller 104 proceeds to step 253 and determines if the caregiver has dismissed the reminder or turned off the desired arming state for system 150. For example, if controller 104 determines that the dismiss control 188 on the monitoring system reminder screen 182 has been selected, then controller 104 proceeds to step 255. At step 255, controller 104 clears the reminder screen 182. The clearance of the reminder screen allows the caregiver to operate user interface 62, including display 64*a*. From step 255, the controller 104 proceeds to step 260 (FIG. 12A)

If, at step 253 (FIG. 12C), controller 104 determines that the off control 186 on the monitoring system reminder screen 182 has been selected, then controller 104 proceeds to step 257. At step 257, controller 104 clears the reminder screen from display 64*a* and clears the desired arming state for monitoring system 152 in memory 106. Thus, off control 186 provides a supplemental manner for a caregiver to change the desired arming state of system 152 (in addition to global setting control screen 190 (FIG. 11)). The desired arming state of system 152 can also be changed using bed monitor control screen 350 (FIG. 17, described in more detail below). In some aspects, the change to the desired arming states made at step 257 carries over to all future iterations of algorithm 200 until a new patient is assigned to patient support apparatus 30. In other aspects, the change to the desired arming states made at step 257 carries over to all future iterations of algorithm 200, including new patients that are assigned to patient support apparatus 30. From step 257, controller 104 proceeds to step 260 (FIG. 12A).

From step 254, controller 104 proceeds to step 260 (FIG. 12A). At step 260, controller 104 determines if all of the conditions in the set of conditions that are monitored for purposes of issuing reminders are in their respective desired states. In the particular aspect shown in FIGS. 12A-12C of algorithm 200, this includes checking to see if brake 61 is activated, if nurse call interface 122 is coupled to nurse call outlet 126, if power cable 112 is plugged into an electrical outlet, if network transceiver 116 is in communication with network 120, if exit detection system 150 is armed, and if monitoring system 152 is armed. If the answer to all of these question is yes (i.e. all of these components are in their desired states), controller 104 proceeds to step 262 and stops the pulsing of lights 68, 78*a*, 78*b*, and 102 (to the extent they were previously pulsed). From step 262, controller 104 returns to step 202 and repeats the execution of algorithm 200. If the answer to the question at step 260 is no (i.e. at least one of the components is not in its desired state), controller 104 skips step 262 and returns to step 202 where it repeats the execution of algorithm 200. It can therefore be seen from steps 260 and 262 that controller 104 only ceases the pulsing of the lights 68, 78a, 78b, and 102 when patient support apparatus 30 has all of its components properly configured. In some aspects, algorithm 200 may be modified to only check the desired arming state for exit detection system 150 or may only check the desired arming state for monitoring system 152.

When controller 104 repeats algorithm 200 (i.e. starts at step 202 for a second or subsequent time), controller 104 does not re-display any of the reminder screens that it previously displayed during a previous iteration of algorithm 200, unless display 64a has been put to sleep between the initial display of the reminder screen and the subsequent iteration of algorithm 200, or the exit detection system 150 and/or the monitoring system 152 have been armed since the previous iteration. In this manner, the caregiver is not presented with the same reminder screen re-appearing during a given session of display 64a being awake unless the caregiver has armed the exit detection system 150 and/or the monitoring system 152. Instead, the reminder screen(s) only appear once and then never appear again so long as display 64a remains in the wake mode and the caregiver has not turned the reminder off and on again by re-arming either of the systems 150, 152. The caregiver is therefore presented with a particular reminder screen only once while continuously utilizing display 64a (e.g. using it sufficient to keep it awake) unless the caregiver re-arms either of the systems 150, 152 during usage, which reminds the caregiver but, other than the single time the reminder screen is displayed, does not interfere with the caregiver's usage of display 64a and/or user interface 62.

In some aspects, the patient support apparatus 30 only includes the exit detection system 150 or only includes the monitoring system 152. In other aspects, the patient support apparatus includes the exit detection system 150 and the monitoring system 152 in combination with each other and/or other monitoring systems.

In one aspect, controller 104 activates lights 68, 78a-b, and 102 when the exit detection reminder and/or the monitoring system reminder are triggered. In many aspects, controller 104 also activates lights 68, 78a-b, and 102 in additional situations beyond those specifically discussed above. For example, in one aspect, controller 104 is configured to flash lights 68, 78a-b, and 102 once (such as in a green color) when any one of the following occurs: (1) support frame 36 is lowered to its lowest height; (2) back section 41 is pivoted to its threshold HOB angle (e.g. 30 degrees, 45 degrees, etc.); (3) a weight reading has been successfully taken of the patient's weight, and (4) equipment has been successfully added to, or removed from, a weight log maintained by patient support apparatus 30 of non-patient weight(s). With respect to this last function (adding and removing weight from a weight log), controller 104 and/or another controller onboard patient support apparatus 30 may be configured to implement an add/remove weight log function, several examples of which are disclosed in commonly assigned U.S. patent application Ser. No. 62/885, 954, filed Aug. 13, 2019, by inventors Kurosh Nahavandi et al. and entitled PATIENT SUPPORT APPARATUS WITH EQUIPMENT WEIGHT LOG, the complete disclosure of which is incorporated herein by reference. Other types of weight log add/remove functions may alternatively or additionally be used.

In some aspects, controller 104 is also configured to activate lights 68, 78a-b, and 102 in a steady, green color when both exit detection system 150 and monitoring system 152 are armed (or only one of these is armed if the user has utilized screen 190 of FIG. 11 to change the desired arming state—stored in memory 106—of the other one of these systems to be a disarmed state). This steady, green activation of lights 68, 78a-b, and 102 only occurs when all of the reminder conditions are in their proper state. Thus, the caregiver will see a steady green light around most of the external perimeter of patient support apparatus 30 only when patient support apparatus 30 has been properly configured and the desired systems 150, 152 have been armed. The steady green light therefore provides an easily visible confirmation to the caregiver that everything on the patient support apparatus 30 has been properly configured, and the lack of the steady green light (e.g. a pulsing amber light, or some other illumination state) indicates that the patient support apparatus 30 is not completely configured in its desired manner.

Lights 68, 78a-b, and 102 are also used to indicate when an alert condition is detected by exit detection system 150 and/or monitoring system 152. When exit detection system 150 detects that a patient has exited from patient support apparatus 30, controller 104 flashes lights 68, 78a-b, and 102 in a red color. When monitoring system 152 detects that one or more of the components monitored by system 152 are in an undesired state, controller 104 flashes lights 68, 78a-b, and 102 in an amber color. Still other manners of using lights 68, 78a-b, and 102 may also or alternatively be implemented.

In addition to controlling lights 68, 78a-b, and 102, controller 104 is further configured, in at least some aspects, to control a light positioned behind brake control 92 on side rail user interface 80 (FIG. 3). In such aspects, controller 104 may be configured to pulse this light in an amber color, and to do so in synchrony with the pulsing of lights 68, 78a-b, and 102, when brake 61 is deactivated. Additionally, controller 104 may be configured to activate this light to a white color when brake 61 is activated (or in some cases, to a green color). If side rail user interface 80 is modified to include additional controls beyond what is shown in FIG. 3 that correspond to any of the conditions that trigger reminder screens (discussed above), controller 104 may be configured to activate lights positioned behind such controls on side rail user interface 80 in the same manners as it activates lights 68, 78a-b, and 102, as discussed above.

In addition to controlling the activation of lights 68, 78a-b, and 102, controller 104 may also be configured to control one or more sounds emitted by a beeper and/or the audio playback circuit 146, amp 147, and speaker 148 positioned onboard patient support apparatus 30. In such aspects, controller 104 may be configured to emit a single beep whenever monitoring system 152 is triggered (i.e. detects an undesired condition), whenever the brake 61 is deactivated, whenever the AC power cord 112 is unplugged, whenever support frame 36 is lowered to its lowest height; whenever back section 41 is pivoted to its threshold HOB angle (e.g. 30 degrees, 45 degrees, etc.), whenever a weight reading has been successfully taken of the patient's weight, and whenever equipment has been successfully added to, or removed from, a weight log maintained by patient support apparatus 30 of non-patient weight(s). Controller 104 may additionally, or alternatively, be configured to emit a continuous beeping when exit detection system 150 detects a patient's exit and/or when exit detection system 150 cannot be armed due to, for example, a patient not settling. This continuous beeping is configured to continue until the caregiver corrects the situation and/or turns off the corresponding alerting system 150, 152.

It will be understood by those skilled in the art that algorithm 200 may be substantially modified from what is shown in FIGS. 12A-C. For example, the specific set of conditions for which reminders are issued may be modified. Additionally, the order shown in these figures in which the conditions are checked may be changed. Algorithm 200 may also be changed such that controller 104 makes different selections for which conditions lead to the pulsing of lights 68, 78a-b, and 102 versus which conditions only lead to the display of a light on dashboard 64b. In other words, controller 104 may be configured to pulse lights 68, 78a-b, and 102 when any of the conditions illustrated on dashboard 64b (FIG. 2) are in an undesired state, or in alternative aspects, any subset of these conditions.

Controller 104 may also delay issuing a reminder in response to a change in state of one or more of the monitored features, conditions, or components, such that patient support apparatus 30 does not indicate an undesired state in response to a momentary change in state. For example, the caregiver may deactivate brake 61 momentarily to adjust a position of the patient support apparatus 30, but then immediately reset brake 61 back to being active. This process may take no more than 30 seconds or less. Accordingly, controller 104 may monitor a time period once the state has changed and delay the associated notification of the state change until a predetermined period of time has elapsed. The predetermined period of time may be 5, 10, 15, 20, 25 seconds, or other predetermined period of time.

Prior to algorithm 200, if the exit detection system 150 or the monitoring system 152 was turned off via the corresponding reminder screen, the patient-specific reminder would be off for the rest of the patient's stay and the only way to enable the patient-specific reminder was using a bed zero screen 312 like the one depicted in FIG. 15. The bed zero screen 312 is displayed on display 64a and allows a caregiver or other user to assign a new patient to the patient support apparatus 30. The bed zero screen 312 has a cancel control 314, a no control 316, and a yes control 318. When a user uses the cancel control 314, the bed zero screen 312 is dismissed, the memory 106 retains the patient-specific reminders, and the caregiver can continue to use display 64a and/or user interface 62. When a user uses the no control 316, the bed zero screen 312 is dismissed, the memory 106 retains the patient-specific reminders, and the caregiver can continue to use display 64a and/or user interface 62. When a user uses the yes control 318, the bed zero screen 312 is dismissed, the memory 106 clears the patient specific reminders for both the exit detection system 150 and the monitoring system 152, and the caregiver can continue to use display 64a and/or user interface 62 to set up patient apparatus 30 for the new patient. Algorithm 200 allows the patient-specific reminders for the exit detection system 150 and the monitoring system 152 to be re-set without having to use bed zero screen 312 and erasing all of the other patient-specific data.

Figure 13:
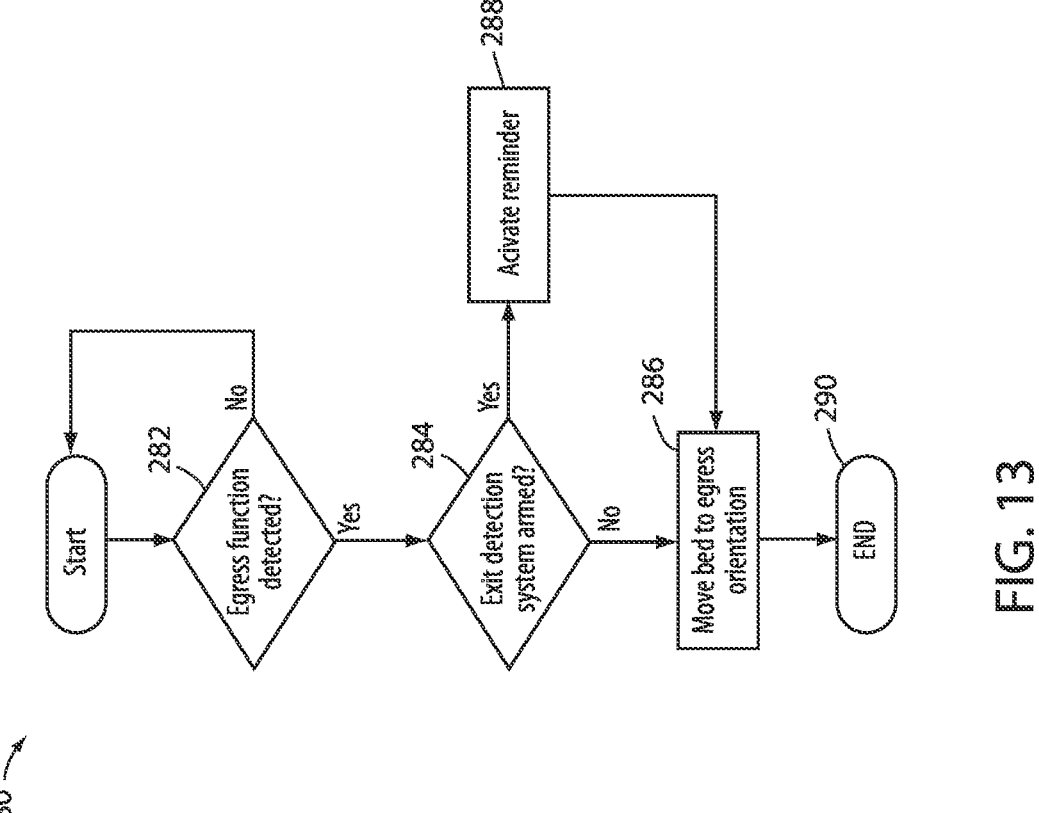
FIG. 13 is an egress reminder algorithm executed by the controller.

In some aspects, patient support apparatus 30 is provided with an egress function, which can be activated by user-activation of egress control 84a on the side rail user interface 80, or optionally via the footboard user interface 62. The egress function allows the caregiver to move the components of support deck 38 and frame 36 into a position that allows easier exit from the apparatus 30, e.g. into an "egress orientation," with the intention that the patient will be exiting the apparatus 30. Accordingly, this can conflict with exit detection system 150 when it is armed, as the egress of the patient detected by the force sensors 130 causes the controller to issue an exit alert. FIG. 13 depicts an egress reminder algorithm 280 that controller 104 follows when the egress function is activated which can remind the caregiver to turn off exit detection system 150 if it is armed to prevent an undesired alert from being issued.

Egress reminder algorithm 280 begins a step 282 when the egress function is activated by the caregiver. Activation of the egress function comprises selection of egress control 84a (FIG. 3) on the side rail user interface 80. From step 282, controller 104 proceeds to step 284 and determines whether exit detection system 150 is armed or disarmed. If exit detection system 150 is disarmed, controller 104 proceeds to step 286 and moves the patient support apparatus 30 to the egress orientation. User-activation of egress control 84a transmits a signal to controller 104 that causes controller 104 to operate the actuators to move the support frame 36, patient support deck 38, patient support surface 42, and/or one or more deck sections 41, 43, 45, 47 to a position that allows the patient to exit the patient support apparatus 30 more easily. For example, controller 104 can raise the back section 41 and lower the support frame 36, patient support deck 38, and patient support surface 42 relative to the base frame 35, including to a lowest height relative to the base frame 35.

In aspects of patient support apparatus 30 with powered side rails 44, 46, 48, 50, user-activation of egress control 84a can also result in moving one or more of the side rails 44, 46, 48, 50 in a manner to facilitate patient egress from the patient support apparatus 30, such as raising or lowering one or more of the side rails 44, 46, 48, 50 and/or re-orienting one or more of the side rails 44, 46, 48, 50 to make patient egress easier.

If exit detection system 150 is armed, from step 284 controller 104 proceeds to step 288 and activates the reminder light 94 and/or lights 102 in order to remind the caregiver to disarm exit detection system 150 prior to the patient egressing from the apparatus 30. The reminder at step 288 may also send an alert to the nurse station via a 37-pin connector or may alert wirelessly. If the patient egress was not intended by the caregiver, the reminder can also serve to alert the caregiver that an egress is occurring. After activation of the reminder light 94 and/or lights 102, controller 104 proceeds to step 286 and moves the patient support apparatus 30 to the egress orientation.

Once the patient support apparatus 30 is in the egress orientation, controller 104 proceeds to step 290 and the algorithm 280 ends. If, at any point after illumination of the reminder light 94 and/or lights 102, exit detection system 150 is disarmed, such as by user-activation of the arming/disarming control 96, controller 104 is configured to turn off the reminder light 94 and/or lights 102.

To the extent not already described, the different content and functions of the various control screens of patient support apparatus 30 may be used in combination with each other as desired, and/or the content and/or functions of one control screen may be applied to one or more other control screens. Further, the selected content shown in any particular control screen herein is not to be construed that it must have all of the content shown therein. For example, aspects including the exit detection system, the monitoring system, the user interfaces, the reminder screens, the reminder management, and the egress function can be implemented independently of each other or in any sub-combination on the patient support apparatus 30.

Various additional alterations and changes beyond those already mentioned herein can be made to the above-described aspects. This disclosure is presented for illustrative purposes and should not be interpreted as an exhaustive description of all aspects or to limit the scope of the claims to the specific elements illustrated or described in connection with these aspects. For example, and without limitation, any individual element(s) of the described aspects may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a support surface adapted to support a patient thereon;
a display;
an exit detection system adapted to be armed and disarmed, the exit detection system adapted to issue an exit alert when the patient exits from the patient support apparatus while the exit detection system is armed;
a memory in which a first setting and a second setting are stored, the first setting indicating whether a reminder to arm the exit detection system is to be issued for all patients and the second setting indicating whether the reminder is to be issued for a specific patient, wherein each of the first and second settings are adapted to be in an on state in which the reminder is issued and an off state in which the reminder is not issued;
a reminder control adapted to allow a user to change the first setting between the on state and the off state;
an arming control adapted to arm and disarm the exit detection system; and
a controller in communication with the display, the memory, the exit detection system, the reminder control, and the arming control, the controller configured to detect when the patient is present on the support surface and to display the reminder on the display if the first setting and the second setting are both in the on state and the exit detection system is not armed, the controller further adapted to override the first setting and not display the reminder on the display if the second setting is in the off state regardless of whether the first setting is in the on state or the off state.

2. The patient support apparatus of claim 1, wherein the controller is further adapted to display the reminder if the first setting is in the off state and the second setting is in the on state.

3. The patient support apparatus of claim 1, wherein the reminder includes a first option to dismiss the reminder and a second option to turn off the reminder, wherein the controller is adapted to remove the reminder when a user-interaction selects the first option, and wherein the controller is adapted to remove the reminder and set the second setting to the off state when a user-interaction selects the second option.

4. The patient support apparatus of claim 1, wherein the arming control automatically switches the second setting to the on state when the exit detection system is armed.

5. The patient support apparatus of claim 1, wherein the reminder control automatically switches the second setting to the off state when the first setting is set to the off state, and wherein the specific patient is a current patient.

6. The patient support apparatus of claim 1, further including:

a new patient control, the new patient control configured to leave the first setting unchanged and automatically change the second setting to the same state as the first setting when the new patient control is activated, and to erase data stored in the memory specific to a current patient.

7. The patient support apparatus of claim 1, further including:
an audio playback circuit in communication with the controller, the audio playback circuit storing at least one audio file to alert hospital staff if the exit detection system is armed and the exit detection system is triggered; and
an amplifier in communication with the audio playback circuit, wherein the amplifier increases the volume of the audio file.

8. A patient support apparatus comprising:
a support surface adapted to support a patient thereon;
a display;
a monitoring system adapted to be armed and disarmed, the monitoring system configured to detect if a component of the patient support apparatus is in a desired state or an undesired state, the monitoring system adapted to issue a monitoring alert when the component is in the undesired state while the monitoring system is armed;
a memory in which a first setting and a second setting are stored, the first setting indicating whether a reminder to arm the monitoring system is to be issued for all patients and the second setting indicating whether the reminder is to be issued for a specific patient, wherein each of the first and second settings are adapted to be in an on state in which the reminder is issued and an off state in which the reminder is not issued;
a reminder control adapted to allow a user to change the first setting between the on state and the off state;
an arming control adapted to arm and disarm the monitoring system; and
a controller in communication with the display, the memory, the monitoring system, the reminder control, and the arming control, the controller configured to detect when the patient is present on the support surface and to display the reminder on the display if the first setting and the second setting are both in the on state and the monitoring system is not armed, the controller further adapted to override the first setting and not display the reminder on the display if the second setting is in the off state regardless of whether the first setting is in the on state or the off state.

9. The patient support apparatus of claim 8, wherein the controller is further adapted to display the reminder if the first setting is in the off state and the second setting is in the on state.

10. The patient support apparatus of claim 8, wherein the reminder includes a first option to dismiss the reminder and a second option to turn off the reminder, wherein the controller is adapted to remove the reminder when a user-interaction selects the first option, and wherein the controller is adapted to remove the reminder and set the second setting to the off state when a user-interaction selects the first option.

11. The patient support apparatus of claim 8, wherein the arming control automatically switches the second setting to the on state when the monitoring system is armed.

12. The patient support apparatus of claim 8, wherein the reminder control automatically switches the second setting to the off state when the first setting is set to the off state, wherein the specific patient is a current patient.

13. The patient support apparatus of claim 8, further including a new patient control, the new patient control configured to leave the first setting unchanged and automatically change the second setting to the same state as the first setting when the new patient control is activated, and to erase data stored in the memory specific to a current patient.

14. The patient support apparatus of claim 8, further including:

an audio playback circuit in communication with the controller, the audio playback circuit storing at least one audio file to alert hospital staff if the monitoring system is armed and the monitoring system is triggered; and an amplifier in communication with the audio playback circuit, wherein the amplifier increases the volume of the audio file.

\* \* \* \* \*